(12) United States Patent
Tanagho et al.

(10) Patent No.: US 6,990,376 B2
(45) Date of Patent: Jan. 24, 2006

(54) METHODS AND SYSTEMS FOR SELECTIVE CONTROL OF BLADDER FUNCTION

(75) Inventors: Emil A. Tanagho, San Raphael, CA (US); Curtis A. Gleason, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 161 days.

(21) Appl. No.: 10/313,960

(22) Filed: Dec. 6, 2002

(65) Prior Publication Data

US 2004/0111126 A1 Jun. 10, 2004

(51) Int. Cl.
*A61N 1/36* (2006.01)

(52) U.S. Cl. .............................. 607/40; 607/74; 607/70
(58) Field of Classification Search .................... 607/40, 607/41, 2, 46, 48, 70, 72, 74
See application file for complete search history.

(56) References Cited

U.S. PATENT DOCUMENTS

| | | | | |
|---|---|---|---|---|
| 2,350,797 A | * | 6/1944 | Morland et al. ............ 331/106 |
| 3,667,477 A | | 6/1972 | Susset et al. | |
| 3,946,745 A | * | 3/1976 | Hsiang-Lai et al. .......... 607/74 |
| 4,057,069 A | | 11/1977 | Dorffer et al. | |
| 4,121,594 A | * | 10/1978 | Miller et al. ................... 607/74 |
| 4,607,639 A | | 8/1986 | Tanagho et al. | |
| 5,038,781 A | | 8/1991 | Lynch | |
| 5,097,833 A | * | 3/1992 | Campos ........................ 607/68 |
| 5,314,458 A | | 5/1994 | Najafi et al. | |
| 5,800,476 A | * | 9/1998 | Piunti .......................... 607/66 |
| 5,824,016 A | | 10/1998 | Ekwall | |
| 5,836,994 A | * | 11/1998 | Bourgeois ..................... 607/40 |
| 6,236,890 B1 | * | 5/2001 | Oldham ........................ 607/68 |
| 6,327,502 B1 | | 12/2001 | Johansson et al. | |
| 6,366,815 B1 | | 4/2002 | Haugland et al. | |
| 6,366,820 B1 | | 4/2002 | Doan et al. | |

* cited by examiner

*Primary Examiner*—Kennedy Schaetzle
(74) *Attorney, Agent, or Firm*—Quine I. P. Law Group, P.C.; Tom Hunter

(57) ABSTRACT

A method and system for selective inhibition of somatic nerve fibers in a mixed nerve containing both somatic and autonomic nerve fibers where the method finds use in treatment of chronic pain, spastic muscles and for sensory and motor control of a bladder. The methods and systems utilize alternate phase rectangular electrical pulses. An electrical pulse generator is coupled to a nerve. An alternate phase high frequency, low amplitude pulse is first applied to selectively inhibit somatic nerves when present in a mixed nerve. An alternate phase low frequency, high amplitude phase pulse subsequently supplied to stimulate the autonomic nerve fibers and in the case of the sacral root will permit a controlled voiding of the bladder and bowel.

34 Claims, 23 Drawing Sheets

METHODS AND SYSTEMS FOR SELECTIVE CONTROL OF BLADDER FUNCTION

CROSS REFERENCE TO RELATED APPLICATIONS

Field of the Invention

This invention relates to methods and systems for regulating neural transmission. Specifically described is a method for selectively inhibiting somatic nerve transmission in a mixed nerve containing both somatic and autonomic nerve fibers. The methods find application in treatment of chronic pain, spastic contractions and for controlling visceral functions. The method directed to the utilization of one or more electrodes on selected nerve bundles and the application of alternate phase rectangular electrical pulses to the electrode(s) to regulate neural transmission or to control muscle contraction.

BACKGROUND OF THE INVENTION

Various medical patients lose voluntary control over their bladder and/or bowel. Although vesicostomy, augmentation cystoplasty or an artificial sphincter implanted around the urethra are commonly used to provide partial control over the evacuation function of the bladder and to control continence, these solutions have drawbacks well known to those skilled in the medical profession and related arts. Other patients who achieve a modicum of control over their bladder functions are equally in need of a system to rehabilitate their nerve and muscle dysfunctions. Similar problems arise in respect to involuntary bowel control.

The physiology of the bladder and bowel is closely linked to the urethral muscle physiology of the pelvic floor (levator and muscle) and its related urethral and anal sphincters. For the bladder to store urine and for the bowel to serve as a reservoir for feces, two opposite, but complementary, behaviors are found. In particular, for storage, the bladder and rectum must relax and the urethral and anal sphincters must remain contracted. The reverse is true during evacuation of either urine or feces, i.e., the urethral or anal sphincter relaxes, along with the pelvic floor, and subsequently the bladder and rectum contracts.

The sequence will reverse once voiding and defecation is completed, i.e., the sphincters and pelvic floor muscles will revert to their tonic closure states and the bladder and rectum will revert to their storage states. This behavior has been demonstrated by simultaneous manometric (or EMG/pressure) recordings of this bladder/rectum, urethral/anal behavior during filling and emptying of the bladder. This sequence of events is well-established and is accepted universally.

Reduced bladder capacity and lack of volitional urinary voiding are experienced by spinal cord injured patients. With the present state-of-the-art, implanted pulse generators that are connected to electrodes attached to sacral roots to electrically stimulate the sacral roots provide patient-controlled bladder voiding. Additionally, dorsal rhizotomies are used to improve the bladder capacity, which is reduced by hyperactivity of the afferent fibers in the dorsal roots.

Currently, voiding by electrical stimulation of the sacral roots is accomplished by stimulating both the somatic and the parasympathetic nerves in the sacral roots. This technique causes both the striated sphincter muscles and the detrusor smooth muscles to contract simultaneously. As a result, the increased sphincter pressure is still able to block the passage of urine in spite of the increased bladder pressure. After a few seconds of stimulation, the electrical stimulus pulses are turned off and the striated somatic muscles relax to decrease the sphincter pressure before the slower smooth muscle of the bladder relaxes, thus providing a pressure differential, higher in the bladder, so that a momentary passage of urine results. The electrical stimulation is again turned on, then off, to obtain another burst of urine. This procedure is repeated until the bladder is effectively emptied.

In most prior nerve stimulators the typical shape of the current or voltage pulses that are used are rectangular and monophasic, that is, current or voltage is one direction. The current (or voltage) is applied for a short duration (typically 0.05 to 2 milliseconds) and then the current (or voltage) supply is turned off, and then turned on again in the same direction. This on-off sequence is continued and produces a train of pulses continued, e.g., at a nominal rate of 20 pulses per second, to stimulate the fibers. Thus, the pulse generators produce essentially monophasic unidirectional pulses of current (or voltage).

SUMMARY OF THE INVENTION

This invention provides a method of selectively inhibiting neural transmission of a somatic fiber in a mixed nerve containing both somatic and autonomic nerve fibers. In one embodiment the method involves applying alternate phase high frequency, low amplitude pulse pairs to the nerve in an amount sufficient to inhibit neural transmission of somatic fibers without inhibiting the autonomic nerves. The method can further involve additionally applying an alternate phase low frequency, high amplitude pulse pairs to the nerve to maintain the inhibition of the somatic fibers while stimulating the autonomic nerve fibers. Preferred frequencies and amplitudes are as described herein.

A preferred use of the invention is to control bladder and bowel function where the method further includes providing an electrical pulse generator. The electrical pulse generator is coupled to at least one nerve responsible for controlling bladder and bowel function. Alternate phase high frequency, low amplitude pulse pairs are applied to the nerve to block sphincter muscle contraction. Low frequency, high amplitude pulse pairs are applied to the nerve to void the bladder or bowel while the alternate phase high frequency, low amplitude pulse pairs are continued. In a preferred embodiment, the low frequency, high amplitude pulse pairs are alternate phase. They may also be monophasic.

Thus, in one embodiment, this invention provides a method of selectively inhibiting neural transmission of a somatic fiber in a mixed nerve containing both somatic and autonomic nerve fibers. The method comprises applying alternate phase high frequency, low amplitude pulse pairs to the nerve in an amount sufficient to inhibit neural transmission of somatic fibers without substantially inhibiting autonomic fibers in said mixed nerve. The method can further comprise applying an alternate phase low frequency, high amplitude pulse pairs to the nerve to inhibit both somatic and autonomic nerve fibers.

In another embodiment, this invention provides a method of controlling a bladder or a bowel. The method involves applying alternate phase high frequency, low amplitude pulse pairs to a nerve that innervates the bowel or bladder; and applying alternate phase low frequency, high amplitude pulse pairs to the nerve to void the bladder or bowel, while continuing to apply the alternate phase high frequency, low amplitude pulse pairs. In certain embodiments, the high frequency pulse pairs are at least 50 pulse pairs per second. In certain embodiments, the high frequency pulse pairs range from about 50 to about 200 or about 80 to about 120 pulse pairs per second (ppps). In certain embodiments, the low frequency pulse pairs are in a range of up to about 40 pulse pairs per second. In certain embodiments, the low frequency pairs are in a range of about 15 to about 25 pulse pairs per second. The amplitude of high frequency pulse pairs typically ranges from about 0.1 milliamperes to about 1.5 milliamperes. In certain embodiments, the amplitude of high frequency pulse pairs ranges from about 0.3 milliamperes to about 0.8 milliamperes. The amplitude of low frequency pulse pairs typically ranges from about 1 milliampere to about 3 milliamperes. In certain embodiments, the amplitude of low frequency pulse pairs ranges from about 1.3 milliamperes to about 1.7 milliamperes. In certain embodiments, the high frequency pulses have pulse widths in a range of about 0.01 ms to about 0.5 ms, more preferably about 0.08 ms to about 0.12 ms. In certain embodiments, the low frequency pulses have pulse widths in a range of about 0.1 ms to about 1.0 ms, and more preferably have pulse widths of approximately 0.5 ms.

This invention also provides a system for controlling a bladder or bowel. The system typically comprises an electrical pulse generator configured to produce alternate phase high frequency, low amplitude pulses and an alternate phase low frequency, high amplitude pulses to a sacral nerve, and at least one electrode that can be coupled to a nerve and transmit an electrical signal from the pulse generator to the nerve. In certain embodiments, the electrode is coupled to the sacral nerve and in electrical communication with the electrical pulse generator. In certain embodiments, the system comprises two electrodes coupled to the electrical pulse generator with four wires. The system can further comprise an external power source electromagnetically coupled to the electrical pulse generator. The system can further comprise a pressure sensitive switch on the electrical pulse generator.

In certain embodiments, this invention also provides a method of inhibiting neural transmission in a nerve by applying electrical impulses to the nerve where the electrical impulses have the following characteristics: alternate phase and a frequency in of at least 60 pulse pairs per second at an amplitude sufficient to inhibit neural transmission. In certain embodiments, the frequency is at least 60 pulse pairs per second. In certain embodiments, the frequency is in a range of about 60 to about 500 pulse pairs per second, more preferably about 60 to about 300 pulse pairs per second.

Also provided is a method of reducing chronic pain. The method involves of applying electrical impulses having the following characteristics: alternate phase and a frequency of at least 60 pulse pairs per second to a nerve at an amplitude sufficient to inhibit neural transmission. In certain embodiments, the frequency is at least 60 pulse pairs per second. In certain embodiments, the frequency is in a range of about 60 to about 500 pulse pairs per second, more preferably about 60 to about 300 pulse pairs per second.

This invention provides a method of reducing muscle spasticity in muscles innervated with nerves. This method involves applying electrical impulses having the following characteristics: alternate phase and a frequency range of at least 60 pulse pairs per second to the nerve at an amplitude sufficient to inhibit neural transmission. In certain embodiments, the frequency is in a range of about 60 to about 500 pulse pairs per second, more preferably about 60 to about 300 pulse pairs per second.

A method is provided for inhibiting neural transmission in nerves by contacting the nerves with an electrode connected to an electrical pulse generator and applying electrical impulses having the following characteristics: alternate phase and a frequency in a range of 60 pulse pairs per second at an amplitude sufficient to inhibit neural transmission. In certain embodiments, the electrode is a ribbon of conducting metal. The nerve can be an intact extradural root. The nerve can be a human nerve or a nerve of a non-human mammal.

In still yet another embodiment, this invention provides a method of controlling a bladder or a bowel. The method involves providing an electrical pulse generator operatively linked to at least one nerve or operatively linking the electrical pulse generator to at least one nerve; applying alternate phase high frequency, low amplitude pulse pairs to the nerve; and applying low frequency, high amplitude pulse pairs to the nerve to void the bladder while continuing to apply the alternate phase high frequency, low amplitude pulse pairs. In certain embodiments, the high frequency pulse pairs are at least 50 pulse pairs per second In certain embodiments, the high frequency pulse pairs range from about 50 to about 200 pulse pairs per second, preferably about 80 to about 120 pulse pairs per second. In certain embodiments, the low frequency pulse pairs are in a range of up to about 40 pulse pairs per second, preferably about 15 to about 25 pulse pairs per second. In certain embodiments, the amplitude of high frequency pulse pairs ranges from about 0.1 milliamperes to about 1.5 milliamperes, preferably from about 0.3 milliamperes to about 0.8 milliamperes. In certain embodiments, the amplitude of low frequency pulse pairs ranges from about 1 milliamperes to about 3 milliamperes, preferably from about 1.3 milliamperes to about 1.7 milliamperes. The high frequency pulses typically have pulse widths in a range of about 0.01 ms to about 0.5 ms, preferably in a range of about 0.08 ms to about 0.12 ms. The low frequency pulses typically have pulse widths in a range of about 0.1 ms to about 1.0 ms. In certain embodiments, the low frequency pulses have pulse widths of approximately 0.5 ms.

This invention also provides a method of stimulating nerve fibers by applying alternate phase pulse pairs.

Also provided is a method of selectively inhibiting neural transmission of somatic nerve fibers while selectively stimulating neural transmission of autonomic nerve fibers in a mixed nerve containing both somatic and autonomic nerve fibers. The method involves applying alternate phase high frequency, low amplitude pulse pairs to inhibit neural transmission of somatic nerve fibers without substantially inhibiting neural transmission of autonomic nerve fibers; and applying alternate phase low frequency, high amplitude pulse pairs to the nerve in an amount sufficient to stimulate neural transmission of autonomic nerve fibers.

In still another embodiment, this invention provides a method of controlling a bladder or a bowel. The method involves (i) applying alternate phase high frequency, low amplitude pulse pairs to inhibit neural transmission of somatic nerve fibers without substantially inhibiting neural transmission of autonomic nerve fibers; and (ii) applying alternate phase low frequency, high amplitude pulse pairs to the nerve in an amount sufficient to stimulate neural transmission of autonomic nerve fibers.

In certain embodiments, the invention provides a system for controlling a bladder or a bowel. The system comprises: at least one electrical pulse generator configured to produce alternate phase low frequency, high amplitude pulse pairs and/or alternate phase high frequency, low amplitude pulse pairs in communication with at least one mixed nerve containing both somatic and autonomic nerve fibers through at least one electrode.

In certain embodiments, this invention provides a system for controlling a bladder or a bowel, the method comprising: at least an electrical pulse generator configured to produce alternate phase low frequency, high amplitude pulse pairs and alternate phase high frequency, low amplitude pulse pairs in communication with at least one mixed nerve containing both somatic and autonomic nerve fibers through at least one electrode.

In still another embodiment, this invention provides a system for controlling a bladder or a bowel. The system typically comprises: at least an electrical pulse generator configured to produce alternate phase low frequency, high amplitude pulse pairs and alternate phase high frequency, low amplitude pulse pairs in communication with a multitude of mixed nerves containing both somatic and autonomic nerve fibers through an array of electrodes.

Definitions

The term "alternate phase" when used with respect to a pulse pair, refers to a pulse pair comprising two pulses of opposite sign, where the potential (for a voltage pulse) or the current (for a current pulse) remains at a common potential or point of no current flow for some measurable time (x in FIG. 1A) between the first and second pulse comprising the pulse pair. In certain embodiments, where the period between the pulse pairs is given by $\lambda$ and the delay between the end of the first pulse of the pulse pair and the beginning of the second pulse of the pulse pair is given by x (see FIG. 1A) then x is preferably equal to or greater than $\lambda/20$, more preferably equal to or greater than $\lambda/10$, and still more preferably equal to or greater than $\lambda/6$ or $\lambda/5$, or $\lambda/3$.

The phrase "a pulse pair comprising two pulses of the opposite sign" refers to a pulse pair where if the first pulse is positive going, the second pulse is negative going and if the first pulse is negative going, the second pulse is positive going.

A "simple biphasic pulse pair" refers to a pair of (electronic) pulses where the first pulse is positive going (current or voltage relative to common) and a second pulse is negative going (current or voltage relative to common) or where the first pulse is negative going and followed by a second positive going pulse and the delay "x" between the first and second pulse is less than $\lambda/20$, more preferably less than $\lambda/40$, or $\lambda/80$ and most preferably is about zero (see, e.g., FIGS. 1A and 1B).

The term "nerve" refers to, but is not limited to, sacral roots, spinal roots, bundles of roots or nerves, mixed fiber nerve bundles, small and large nerve fibers, dorsal roots, ventral roots, somatic nerve bundles and autonomic nerve bundles.

The terms "mixed nerve" or "mixed fiber nerve" or "mixed fiber nerve bundle" are used interchangeably and refer to groups or bundles of nerve axons.

The term "small fibers" refers to nerve fibers having a diameter less than about 2 $\mu$m.

The term "large fibers" refers to nerve fibers generally having a diameter greater than about 2 $\mu$m.

The phrase "operatively linking" when referring to operatively linking a pulse generator to a nerve indicates that the pulse generator is disposed in a manner that permits the application of generated pulses to the nerves. Such operative linking can be accomplished in any of a number of ways, e.g. by connecting the pulse generator via conductive leads to one or more electrodes applied, positioned, juxtaposed next to, inserted into the nerve, nerve root, etc., by direct juxtaposition of the pulse generator to the subject nerves, by radio, magnetic, inductive, or other electromagnetic coupling of the pulse generator to one or more electrodes in contact with the nerves, and so forth.

DETAILED DESCRIPTION

Figure 1A:
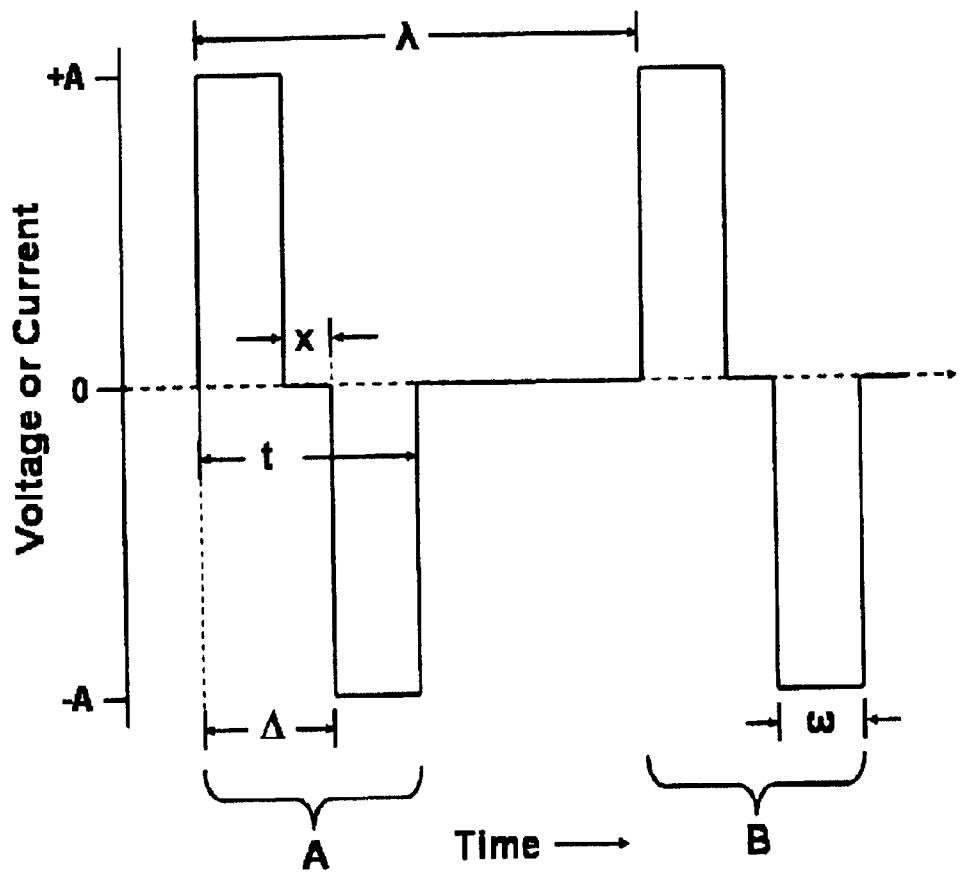
FIGS. 1A and 1B illustrate two alternate phase pulse pairs (A and B) (FIG. 1A) and a two simple biphasic pulse pairs (A and B) (FIG. 1B).

This invention pertains to novel devices and methods for selective control of somatic fibers or autonomic fibers in a mixed fiber nerve. Such mixed fiber nerves innervate various organs such as the bowel and bladder. By selectively regulating autonomic and somatic fiber activity, organ control can be effected where such control has been compromised (e.g. by neurological damage). Thus, for example, bladder and/or bowel retentions and evacuation can be more effectively controlled particularly in subjects where voluntary control is non-existent or inhibited.

I. Selective Control of Large and Small Fibers in a Mixed Fiber Nerve

This invention is based, in part, on the discovery that mixed frequency, alternate phase current or voltage pulses can selectively block impulses in somatic fibers to achieve flaccid paralysis of the sphincter muscles and selectively excite the autonomic fiber(s) to produce detrusor muscle contraction. High frequency, low amplitude current or voltage pulses make the sphincter muscles unresponsive to low frequency, high amplitude current or voltage pulses which contract the detrusor muscles to effectively achieve bladder voiding in spinal cord injured subjects.

This differential activation/inhibition of small and large fibers can readily be exploited in the regulation of bladder (or other organ) function in subjects in which such function is compromised. In particular, the ability to utilize high frequency small amplitude pulse pairs applied, e.g. to a motor root to control sphincter activity, obviates the need for surgical separation, dissection and resection, e.g., of the sacral somatic nerve Ss and possible attendant complications (e.g. incontinence) can thereby be avoided.

More generally, it was discovered that effective differential excitation of large and small fibers in a bundle of mixed nerve fibers can be achieved by the use of alternate phase pulse pairs. In particular, the application of alternate phase high frequency current or voltage pulse pairs is effective in blocking post-synaptic responses, while leaving small fibers essentially unaffected. Mixed frequency, alternate phase current or voltage pulses can selectively block impulses in somatic and selectively excite autonomic fiber(s) in a mixed fiber nerve.

It was also discovered that high current/voltage pulses are able to produce blockage in the smaller fibers, for example, of the autonomic system. Thus, in another embodiment, high current/voltage pulses are used to block small fibers of the autonomic nervous system. This block is also applicable to the efferent and/or afferent fibers, for example, the fibers used in proprioception, pain, and temperature.

This invention thus provides the means for differential activation/inhibition of small and large fibers in a mixed fiber nerve. This differential activation/inhibition of small and large (autonomic and somatic fibers) finds use in a wide variety of contexts. Such differential inhibition/activation can be exploited to provide effective control of bladder function and/or to provide effective control of other organs, such as the bowel, colon and associated sphincters, (e.g., anus). The methods of this invention can also provide means for eliminating or suppressing spastic detrusor activity, spastic urethral and pelvic floor activity and spastic anal sphincter, and the like.

It was also a surprising discovery that, as explained herein, alternate phase pulse pairs are particularly effective in providing selective control of small and large nerve fibers.

In certain embodiments, the stimulation is provided as "alternate phase" voltage or current pulses (see, e.g., FIG. 1A). While the pulse are illustrated as "square wave" pulses in FIG. 1A, they need not be so limited. Other alternate phase waveforms (e.g. sinusoidal, triangular, ramped, stepped, etc.) can also be utilized.

Figure 1B:
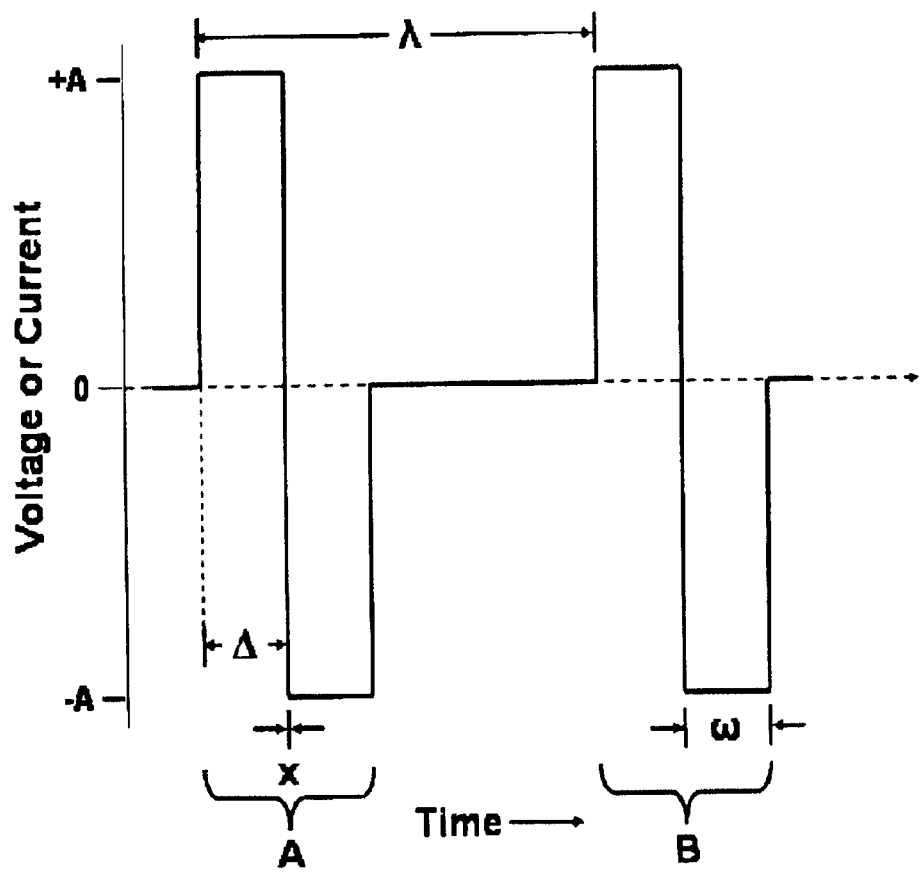

As illustrated in FIG. 1A, an alternate phase pulse pair refers to a pulse pair where the potential (for a voltage pulse) or the current (for a current pulse) remains at a common potential (or no current) for some measurable time between the first and second pulse. This is in contrast to the typical biphasic pulse pair or biphasic pulse (illustrated in FIG. 1B) where there is essentially no delay at common or ground between the first and second phase of the pulse pair. In addition, when the first pulse is positive going, the second pulse is negative going and when the first pulse is negative going, the second pulse is positive going.

The pulse pair is characterized by a frequency f or period λ (time between pulse pairs), an amplitude (current or voltage), a pulse width w, a time between the beginning of the first phase/pulse in a pulse pair and the beginning of the second phase of the pulse pair Δ, a time between the end of the first phase of a pulse pair and the beginning of the second phase of a pulse pair x, and/or a pulse pair duration t as illustrated in FIG. 1A.

In accordance with one aspect of this invention, high frequency low amplitude pulse pairs are used to disable large fibers and thereby inhibit skeletal muscle activity (e.g. to paralyze sphincters). In certain embodiments, a high frequency pulse pair has a frequency f of at least about 50 pulse pairs/second up to a frequency of about 200 to 300 pulse pairs per second. In typical embodiments, the frequency is in a range of about 60 to about 500 pulse pairs per second, preferably about 60 to about 200 pulse pairs per second, more preferably about 80 to about 150 pulse pairs per second, and most preferably from about 90 to about 120 pulse pairs per second.

In accordance with one aspect of the present invention, the low frequency pulse pairs range from about 10 pulse pairs per second up to about 40 pulse pairs per second. In certain embodiments, the low frequency pulse pairs range in frequency from about 15 to about 25 pulse pairs per second.

The high frequency pulses typically have pulse widths w ranging from about 0.01 ms to about 0.5 ms, preferably from about 0.01 ms to about 0.20 ms, more preferably from about 0.02 ms to about 0.15 ms, and most preferably from about 0.08 ms to about 0.12 ms.

The low frequency pulses typically have pulse widths raging from about 0.1 ms to about 1 ms, preferably from about 0.2 ms to about 1.0 ms, and most preferably have pulse widths of approximately 0.5 ms.

The pulse pairs used in the methods of this invention can vary in amplitude, as well as frequency f, width w, and delay Δ or x. As indicated herein, high frequency low amplitude pulse pairs are used to disable (inhibit) large fiber activity. The low amplitude pulses range from about 0.1 milliamps to about 1.5 milliamps or range from a voltage sufficient to produce a current of about 0.1 milliamps to about 1.5 milliamps. In certain embodiments, the low amplitude pulses range from about 0.3 to about 1.0 milliamps, preferably from about 0.4 to about 0.9 milliamps, more preferably from about 0.4 to about 0.8 milliamps.

High amplitude, low frequency pulse pairs are used to activate small fibers (e.g. to evacuate bowel or bladder). In accordance with this invention, high amplitude pulse pairs range in amplitude from about 1.0 to about 3.0 milliamps or range from a voltage sufficient to produce a current of about 1.0 to about 3.0 milliamps. In certain embodiments, the high amplitude pulse pairs rang in amplitude from about 1.3 to about 1.7 milliamps.

Figure 2:
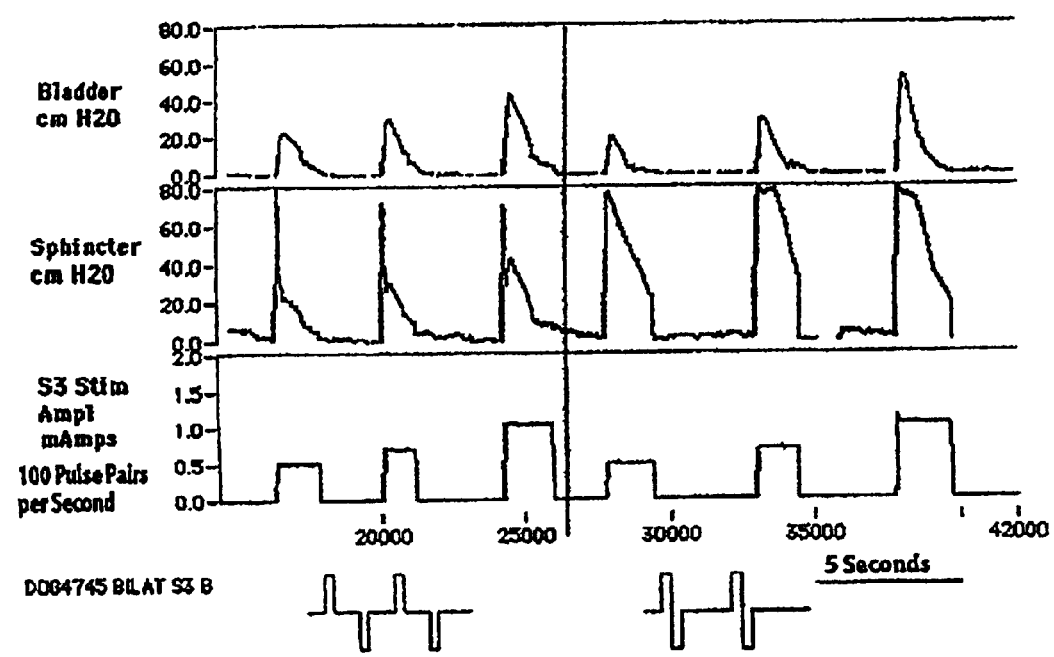
FIG. 2 shows graphs that compare the effects of two different pulse patterns on sphincter pressure.

It was a surprising discovery that alternate phase pulse pairs provide improved efficacy in regulating bladder function and/or the function of other organs. As illustrated in FIG. 2 the effects of alternate phase pulses on sphincter pressure are different compared with the effects produced by the "biphasic" pulses. The pulse patterns are shown at the bottom of the figure. On the left are two "alternate phase" pulse pairs and on the right are two simple "biphasic" pulse pairs. The pulse rate of each pattern is 100 pulse pairs per second. Each pattern was turned on for about 2.5 seconds at three different current amplitudes: 0.5, 0.7, and 1.0 milliamperes, as shown on the bottom trace. The effect of the stimulation is shown in the top two traces.

The bladder pressures are similar for the two different pulse patterns. The sphincter pressures, however, are different. The "alternate phase" pulses produce a very short, high-pressure burst in the sphincter followed by the bladder pressure that is reflected in the sphincter area. The simple "biphasic" pulses produced a prolonged sphincter pressure that was always higher than the bladder pressure during the period of stimulation. The "alternate phase" pulses relaxed the sphincter immediately so that voiding could be initiated far sooner than would be possible with the "biphasic" pulses. Thus, greater bladder voiding was obtained with lower sphincter pressure.

The delay x between the two pulses comprising the pulse pair is typically optimized to produce maximum efficacy (e.g., of bladder voiding). Typically, the most desirable effect is produced by the symmetrical "alternate phase" pulse pair, that is, equal time between the plus and minus and minus and plus phases. As the "alternate phase" pulse pair becomes closer to a simple "biphasic" pulse pair the effect (e.g. x approaches zero) the enhanced effect shifts accordingly.

In various embodiments, of the present invention, the "alternate phase" pulse pair ranges from equal timing (2:1 ratio $\lambda/x$) between phases to about a 4:1, 6:1 or 8:1 ratio ($\lambda/x$). Thus, for example, if $\lambda$ is the time between two plus phases, then a symmetric wave form will be obtained with $x=\lambda/2$. While $\lambda$ and x are illustrated with respect to the leading edge of the pulse(s) (see, e.g., FIG. 1A), they could also be measured with respect to the midpoint of the pulse or with respect to any other convenience reference point.

The pulse amplitude A, frequency f, delay x, $\Delta$, and width w can be optimized for maximum efficacy in each subject. Typically, this is accomplished after surgical placement of the electrodes. In certain embodiments, a programmable controller is used to vary these parameters as well as electrode selection/activation in multiple electrode configurations to achieve maximum efficacy. If possible, a configuration that produces maximum efficacy with minimal power consumption is selected.

It is noted that, while the alternate phase pulse pairs are illustrated with both pulses comprising the pair having the same width w and amplitude A, these parameters can be individually varied for each pulse.

In brief summary, high frequency, low amplitude pulse pairs, preferably alternate phase pulse pairs act to disable the function of organs innervated by larger fibers. Such pulse pairs, can be used to flaccidly paralyze sphincter muscles without activating small fibers. Low frequency, high amplitude pulse pairs, preferably alternate phase pulse pairs activate small fibers. High frequency, high amplitude pulse pairs, preferably alternate phase pulse pairs, act to selectively block small fibers. These effects are summarized in Table 1.

TABLE 1

Summary of effects of pulse pairs, preferably alternate phase pulse pairs.

| Pulse Type | Effect |
| --- | --- |
| High frequency, low amplitude | Disables large fibers. Flaccidly paralyze sphincter. No effect on small fibers |
| Low frequency, high amplitude | Activate small and large fibers. Activate detrusor muscles. |
| High frequency, high amplitude | Produce blockage in small fibers (e.g. efferent and afferent fibers). Block proprioception, pain, temperature, etc. |

II. Control of Bladder Function

In certain embodiments, this invention provides systems and methods for controlling a bladder (e.g. maintaining continence and/or effecting evacuation when desired). The pulse generation systems of this invention typically include an electrical pulse generator configured to produce alternate phase high frequency, low amplitude pulses and alternate phase low frequency, high amplitude pulses that can be transmitted by one or more electrodes on one or more sacral root(s). The system thus includes at least one electrode that can be coupled to a sacral root and in electrical communication with the electrical pulse generator.

Figure 3:
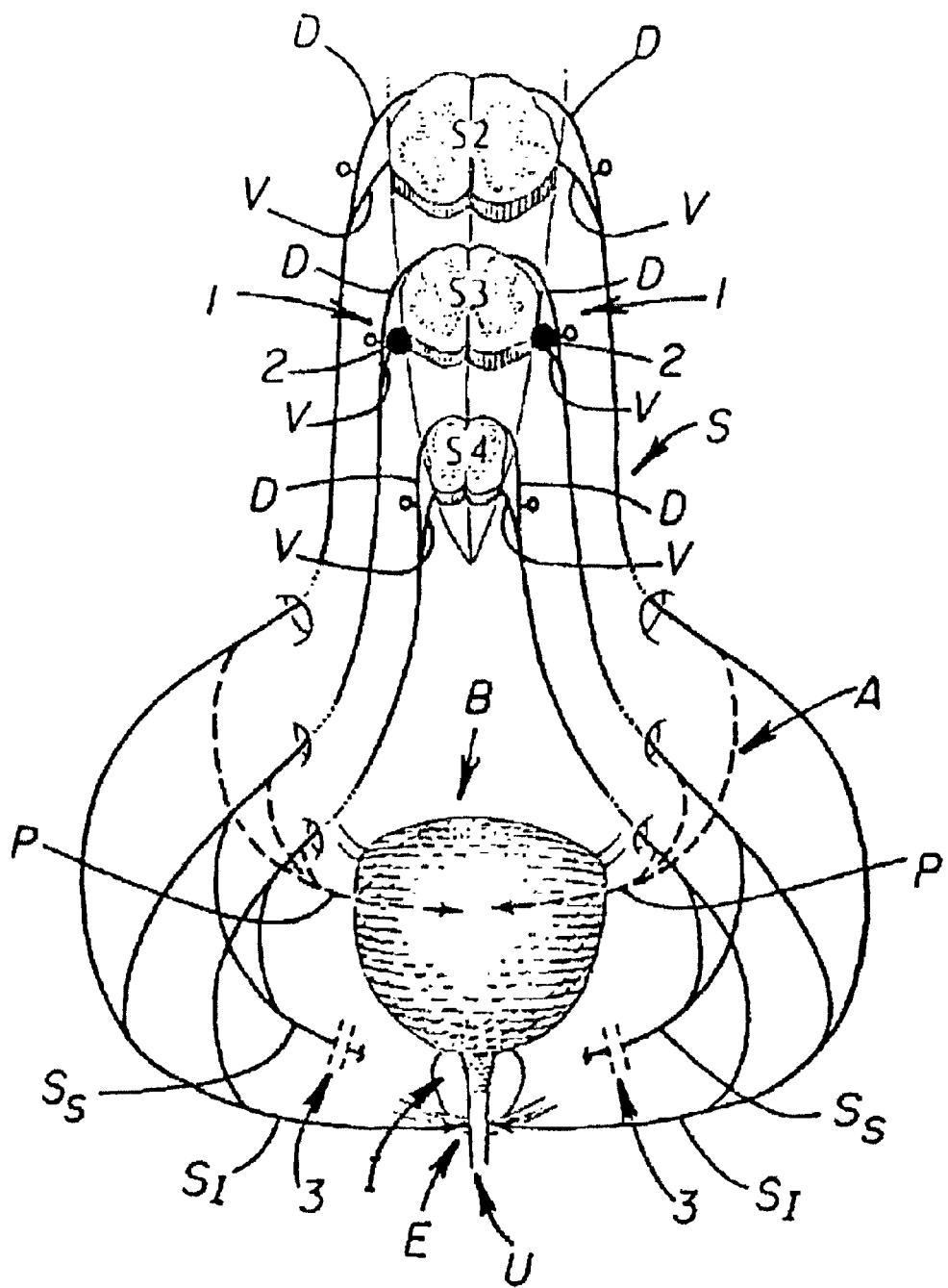
FIG. 3 schematically illustrates the pelvic plexus region in a human, including the nervous system for controlling bladder evacuation and related functions, and further illustrates an operative procedure for controlling such functions.

As described in U.S. Pat. No. 4,607,639, FIG. 3 schematically illustrates the pelvic plexus region of a human, including the nervous system for controlling bladder evacuation and related functions. The nervous system includes a somatic nerve system of fibers (or nerve bundles) S and an autonomic nerve system of fibers or nerve bundles A, finding their immediate origin at sacral segments S2, S3 and S4 of the spinal cord and sacrum. The main nerve supply to the detrusor muscle of a bladder B emanates primarily from sacral segment S3, a lesser amount from sacral segment S2, and a still lesser amount from sacral segment S4.

One aspect of this invention is directed to a method for controlling the evacuation of bladder B. The method can involve identifying the anatomical location of at least one nerve or component thereof that controls at least one function of the bladder, e.g., continence and/or contraction of the bladder. One or more electrodes are then positioned, either surgically or percutaneously, at least in close proximity to the nerve or nerve root and selectively energized as described herein to stimulate particular fibers.

Further, this invention contemplates either permanent surgical implantation or temporary percutaneous of the devices described herein implantation for nerve stimulation purposes.

As further illustrated in FIG. 3, the main nerve supply emanating from each sacral segment S2, S3 and S4 comprises two components or roots, namely, a dorsal root D and a ventral root V. The dorsal root is primarily sensory to transmit sensation to the spinal cord whereas the ventral root is primarily motor to transmit motor impulses from the spinal cord to bladder B and associated sphincter. Although illustrated as being separated, the dorsal and ventral roots for each nerve are, in fact, normally joined together and their fibers mixed to progress as a single trunk.

Fibers of the nerve trunk are divided into somatic fibers S that connect to voluntary muscles and autonomic fibers A that connect to visceral organs, such as bladder B. In various embodiments, methods of this invention involve isolation of various components of these nerve fibers at various levels in the nervous system. Although not required by the devices described herein, dorsal root D can be separated from ventral root V to facilitate stimulation of only the motor fibers of a particular ventral root. In this manner, the motor fibers can be stimulated without inducing pain and without generating impulses along the sensory passage way.

Of course, the use of dual mode (e.g. high frequency low amplitude pulse pairs followed by low frequency high amplitude pulse pairs) pulse pairs as described herein can obviate the need for sectioning ventral root from dorsal root.

Previous methods required that somatic nerves S and autonomic nerves A be separated from each other to effectuate independent stimulation. Indeed to eliminate sphincter activity and facilitate bladder voiding, the sacral somatic Ss nerve is often sectioned bilaterally.

A significant advantage of the devices and methods described herein is the independent inhibition/activation of small and large fibers. Accordingly, using only electronic means, the sphincter muscles can be selectively relaxed while the detrusor muscles are actuated to effectuate bladder voiding. The methods of this invention thus eliminate the need to section somatic nerve and continence is more easily maintained.

In addition, particular pulse trains can be delivered to particular roots to maximize efficacy. For example, responses obtained with pre-operative evaluation of responses to stimulation recorded urodynamically could indicate that the S2 sacral nerve constitutes the main motor supply to external sphincter E, whereas the S3 sacral nerve constitutes the main motor supply to bladder B. Thus, the S3 sacral nerve would be utilized to control the detrusor muscle and thus the contracting function of bladder B and stimulation predominantly with low frequency high amplitude alternate phase pulse pairs as described herein can optimize bladder evacuation. Conversely, in this context, the S2 sacral nerve could be utilized to control the muscles controlling the continence function of external sphincter E and application of high frequency small amplitude pulse pairs predominantly to this root can effectuate sphincter relaxation. Studies have shown that in certain patients, only the nerves on one side of the sacrum provide the main motor control over a particular organ, i.e., unilateral control rather than bilateral control. Pre-operative testing of a particular patient can determine which variation will provide the best choice for a subsequent operative procedure. The ability of this invention to selectively activate or inhibit particular components of the various nerves or roots, with the combined ability to test a patient intraoperatively and record responses enables the surgeon to isolate and selectively stimulate the particular nerve fibers that will effect the specific function or functions required.

Figure 4:
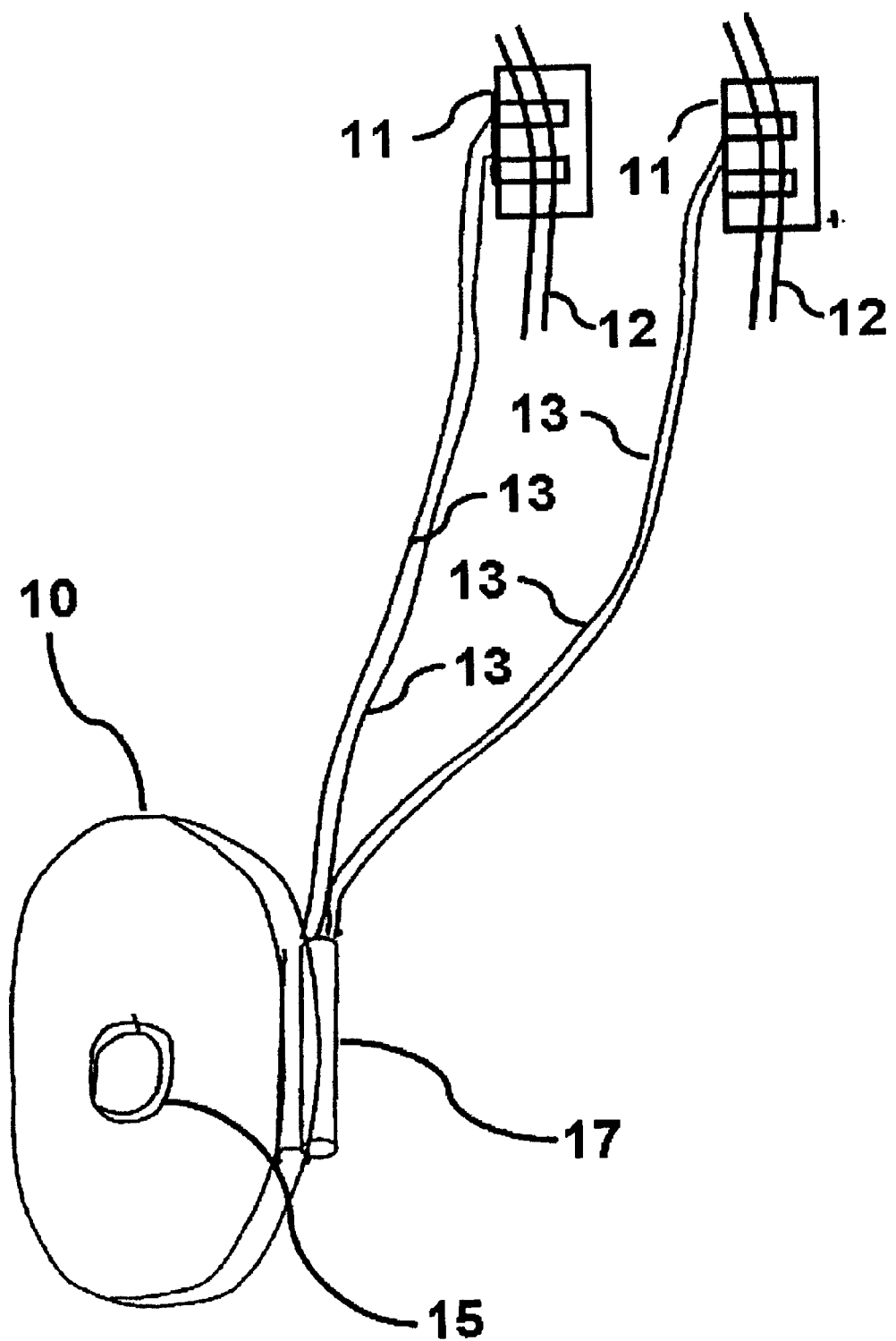
FIG. 4 illustrates an implantable pulse generator 10 operably linked to nerves 12 via leads 13.

FIG. 4 illustrates an implantable pulse generator 10 activated by a pressure sensitive switch 15. One example of a generator includes a battery to provide power to the circuits. Electrodes 11 that attach to nerves 12 are shown with their leads 13 connected to the pulse generator, e.g. via connector 17 (e.g. a 4 wire connector).

Figure 5:
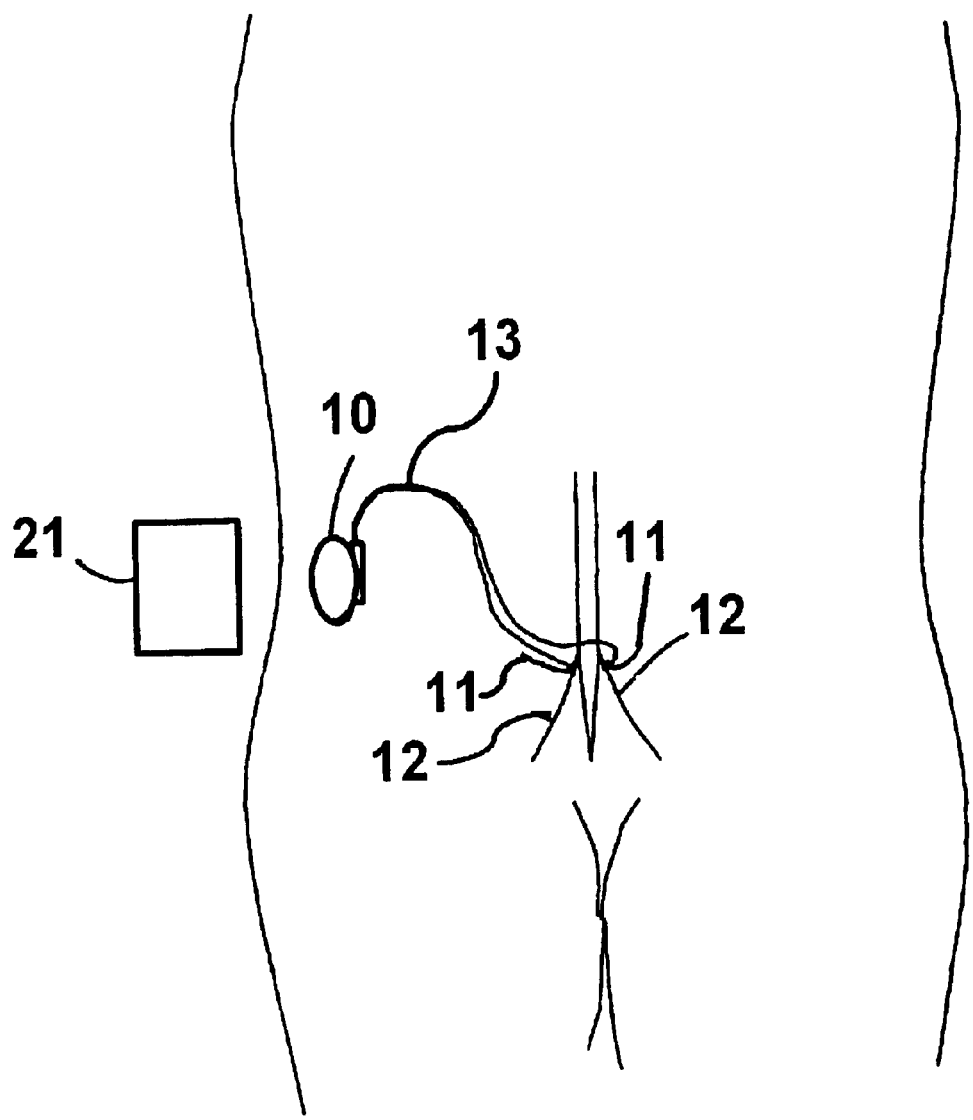
FIG. 5 is schematic illustration of a system for controlling a bladder in accordance with the present invention.

FIG. 5 illustrates an example of placement of the electrodes and pulse generator inside a patient. Preferably, there are several electrodes, one or more for each nerve root. After the electrodes are placed around appropriate sacral roots 12, leads 13 are brought around to the implantation site of the pulse generator. The leads are preferably attached to the pulse generator via mating connectors on the leads and the pulse generator. In certain embodiments, the implanted pulse generator is programmed via an external controller 21 that communicates with the implant 10 by coded electromagnetic pulses. The external device can be held over the site of the implant to accomplish the programming. After the implant is programmed, the implant can be activated (e.g. by electromagnetic pulses, a magnet, by manually operating a pressure-sensitive switch, etc.).

The electrodes can be applied to any nerve including roots such as the sacral root and peripheral nerves such as the sciatic nerve. Contact can be anywhere along the nerves including intradurally and extradurally. In preferred embodiments contact is at the sacral roots, more preferably at a plurality of sacral roots, e.g. using an electrode array.

In accordance with the present invention, when the implant is activated it generates continuous high frequency, low amplitude, "alternate phase" pulses, i.e., alternate phase pulse pairs, that are applied to the nerves via the leads and electrodes to selectively inhibit neural transmission in somatic fibers.

In cases where bladder capacity is adequate and the bladder is not too spastic, bladder voiding is accomplished using high frequency, low amplitude alternate phase pulses to render the sphincter unresponsive to subsequently applied low frequency, higher amplitude pulses that induce contraction of the bladder detrusor muscles. The pulse pairs are typically applied to one or more dorsal roots.

Figure 6A:
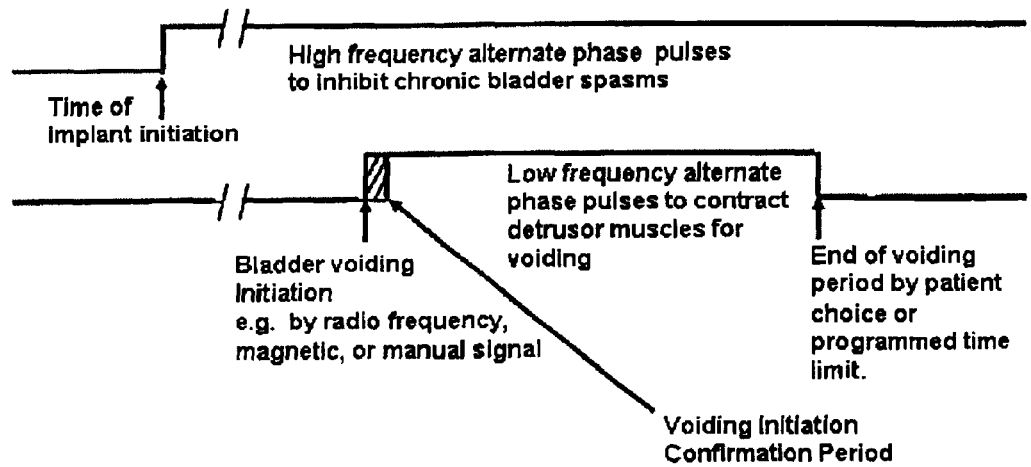
FIGS. 6A and 6B are examples of a pattern for pulses for controlling a bladder in accordance with the present invention.
Figure 6B:
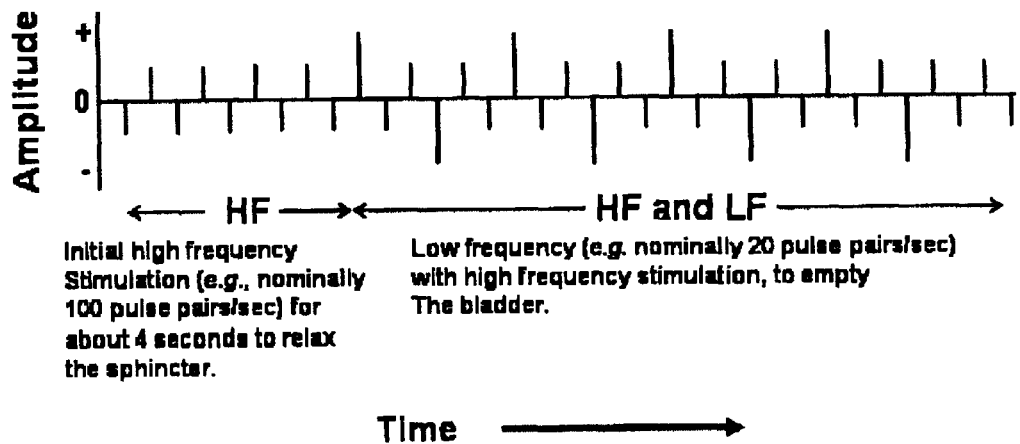

A typical pulse pattern to effect bladder evacuation is illustrated in FIGS. 6A and 6B. Initial high frequency low amplitude stimulation (e.g., nominally 100 pulse pairs/sec) for about 1 to about 10 seconds, more typically from about 2 to about 6 or 8 seconds, and most typically for about 4 seconds 4 seconds disables transmission in somatic fibers that innervate the sphincter muscles and produces sphincter relaxation. The application of a second electrical signal comprising low frequency high amplitude pulse pairs (e.g. nominally 20 pulse pairs/sec) then stimulates bladder contraction to effect evacuation. While the high frequency, low amplitude alternate phase pulses are present, the sphincter is not responsive to the low frequency, higher amplitude pulses and thus does not impede the flow of urine and the bladder empties in a continuous stream. Both the high frequency, low amplitude and the low frequency, higher amplitude pulses are turned off either after a preset time in the pulse generator or by the patient.

This second electrical signal can be delivered via different electrode(s) than the electrode(s) delivering the low amplitude, high frequency pulse pairs and/or it can be delivered on the same electrode(s). The second electrical signal can be generated from a separate generator than that generating the first electrical signal, or both electrical signals can be generated by the same pulse generator. That is the signals can be separate or overlaid in a complex signal from a single generator. Where both signals are delivered by the same electrode or electrode pair, in certain embodiments, one of the low amplitude pulses of the high frequency pulse train higher is periodically increased in amplitude (to produce the low frequency high amplitude signal). The periodicity of these higher amplitude pulses is preferably the inverse of the effective frequency of the desired low frequency pulses In the case of spasticity in the bladder, e.g., bladder hyperactivity, the alternate phase pulse generator systems of this invention can be used to increase bladder capacity. The application of the high frequency, high amplitude alternate phase pulses blocks impulse transmission in the dorsal roots, thus releasing the bladder spasticity to allow the bladder to fill. The high amplitude of the high frequency pulses blocks the transmission of impulses in the smaller fibers associated with the sensory fibers from the bladder. (These high amplitude high frequency pulses also block impulse transmission in the larger somatic fibers.)

While it is preferable that the low frequency, high amplitude pulse pairs are alternate phase, it is not required. The low frequency, high amplitude pulse pairs can be simple biphasic pulse pairs or even monophasic.

When it is desired to void the bladder, reducing the amplitude of the high frequency alternate phase pulses allows the smaller fibers to recover and to transmit their impulses from the bladder to the spinal cord, thus causing the bladder to become spastic and increasing the bladder pressure. The resulting increased bladder pressure along with the continued blocking of the sphincter muscles by the lower amplitude high frequency alternate phase pulses allows the bladder to empty. In addition, low frequency high amplitude pulse pairs can activate the detrusor muscles effecting bladder evacuation. At the completion of bladder emptying the amplitude of the high frequency can increased after a predetermined time of by the patient (or patient's attendant) to again reduce spasticity.

In the instance of a patient desiring to empty a bladder, the operator (e.g., patient, attendant, doctor, etc.) activates the pulse generator e.g. using an external actuator (radio controller, magnetic controller, induction controller, etc.) or by manipulation of an implanted pulse generator (e.g. by locating the bulge of the pressure sensitive switch located on the implanted pulse generator). In certain embodiments, the operator is required to press the switch on the pulse generator or on the controller in a coded manner in order to prevent accidental activation of the implant. For, example, pressing the switch for one second then releasing the switch for a second and then pressing the switch for more than two seconds may activates the voiding cycle.

In certain embodiments, the system can provide feedback to the operator (e.g. via a signal to the controller) to indicate that the sphincter is relaxed and detrusor muscles are ready to be activated. The activation of the detrusor muscles can then be manual (e.g., under control by the operator), or automatic/timed.

In certain embodiments, the device can signal the operator when the void cycle is completed, can complete the void cycle at a present time, or in response to a signal (e.g. a pressure signal, a proprioceptive signal, etc.). Termination of the voiding period may be either automatic or manual. The implant may be programmed to turn off the high amplitude, low frequency, and "alternate phase" pulses after a period of time (e.g. fifteen seconds). Alternatively, the patient may stop the voiding period sooner by pressing the switch that is on the implant. For example, a simple stop signal may be continuous depression of the switch for at least 3 seconds.

III. Other Uses for the Methods and Devices of This Invention

A) Control of other organs.

As the bowel and colon are also controlled by sacral roots, the methods described above to effect bladder evacuation can also be used to effect evacuation of the bowel or colon. Basically colon evacuation is effected by administering a high frequency, low amplitude current or voltage pulses to appropriate nerve root(s) to relax the external sphincter (anus). Then a low frequency, high amplitude current or voltage pulses is superimposed on the first signal to produce contraction of muscles to effectively achieve evacuation of the colon. Bowel evacuation can similarly be accomplished.

Bladder, bowel, or colon evacuation can be concurrently or independently as desired and determined by the particular clinical presentation.

B) Blockage of pain, proprioception, temperature, muscle spasticity and the like.

As explained herein, high frequency, high amplitude electrical stimulation (e.g. of nerve roots) can produce blockage in small fibers. This is effective in both efferent and afferent fibers.

Blockage of efferent fibers can be exploited in a wide variety of contexts. For example where a bladder, bowel or colon is spastic, the spasticity prevents complete filling of the subject organ. Administration of high frequency, high amplitude electrical stimulation to the appropriate nerve roots can inhibit small fiber activity and thereby suppress the spasticity permitting proper filling of the subject organ.

Blockage of afferent fibers can inhibit sensory nerves, e.g. proprioception pain, temperature, and the like. This can be exploited to treat chronic pain (e.g. severe arthritis, chronic back pain, neuropathy, and the like).

Typically, as indicated above, blockage of small fibers is accomplished by administering a high frequency high amplitude alternate phase electrical stimulation to one or more nerve roots, e.g., as described herein. In certain embodiments, the impulses are alternate phase impulses with a frequency of at least 60 pulse pairs per second at an amplitude sufficient to inhibit neural transmission. The nerve is optionally a mixed nerve having both somatic and autonomic nerve fibers.

IV. Devices and Electrodes for the Selective Control of Large and Small Fibers

Devices and electrodes for generating and applying alternate phase pulse pairs according to this invention can take a wide variety of embodiments. Typically such devices comprise a pulse generator for generating the current or voltage pulse pairs, and one or more electrodes for conducting the pulse pairs to the site of pulse application, usually a nerve root.

A) Pulse generator.

The alternate phase pulse pairs used in the methods of this invention are typically created by a pulse generator. In certain embodiments, the pulse generator is implantable (within the body of the subject) (e.g. subcutaneous or visceral) while in certain embodiments, the pulse generator is external.

Figure 7:
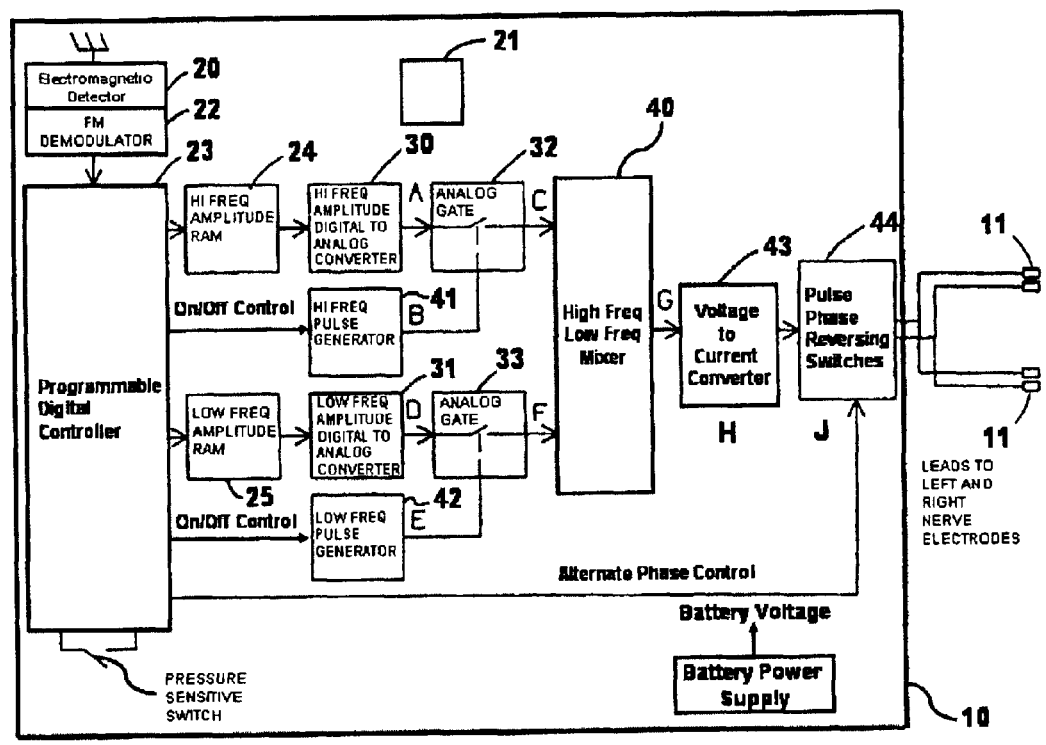
FIG. 7 is a block diagram illustrating an example of an implantable pulse generator in accordance with the present invention.

FIG. 7 illustrates a block diagram of an implantable pulse generator 10. The pulse generator comprises a control system adapted to transmit electrical current pulses to electrodes implanted on selected nerves or nerve roots as described herein. The control system comprises an external control-transmitter system 21 and a receiver system 20 implanted on a patient for transmitting electrical current pulses to the electrodes. The purpose of the illustrated system is to efficiently provide high frequency low amplitude alternate phase pulse pairs to disable large fibers with the subsequent addition of low frequency high amplitude pulse pairs to effect small fiber activity.

An electromagnetic detector 20 receives electromagnetic emissions from an external transmitting device 21. The emissions are preferably a series of electromagnetic pulses that are coded according to information that is sent to the implant. An FM detector 22 converts the electromagnetic pulses into voltages that can be used by a micro-controller 23 to perform operations that are sent from transmitter 21.

Figure 8:
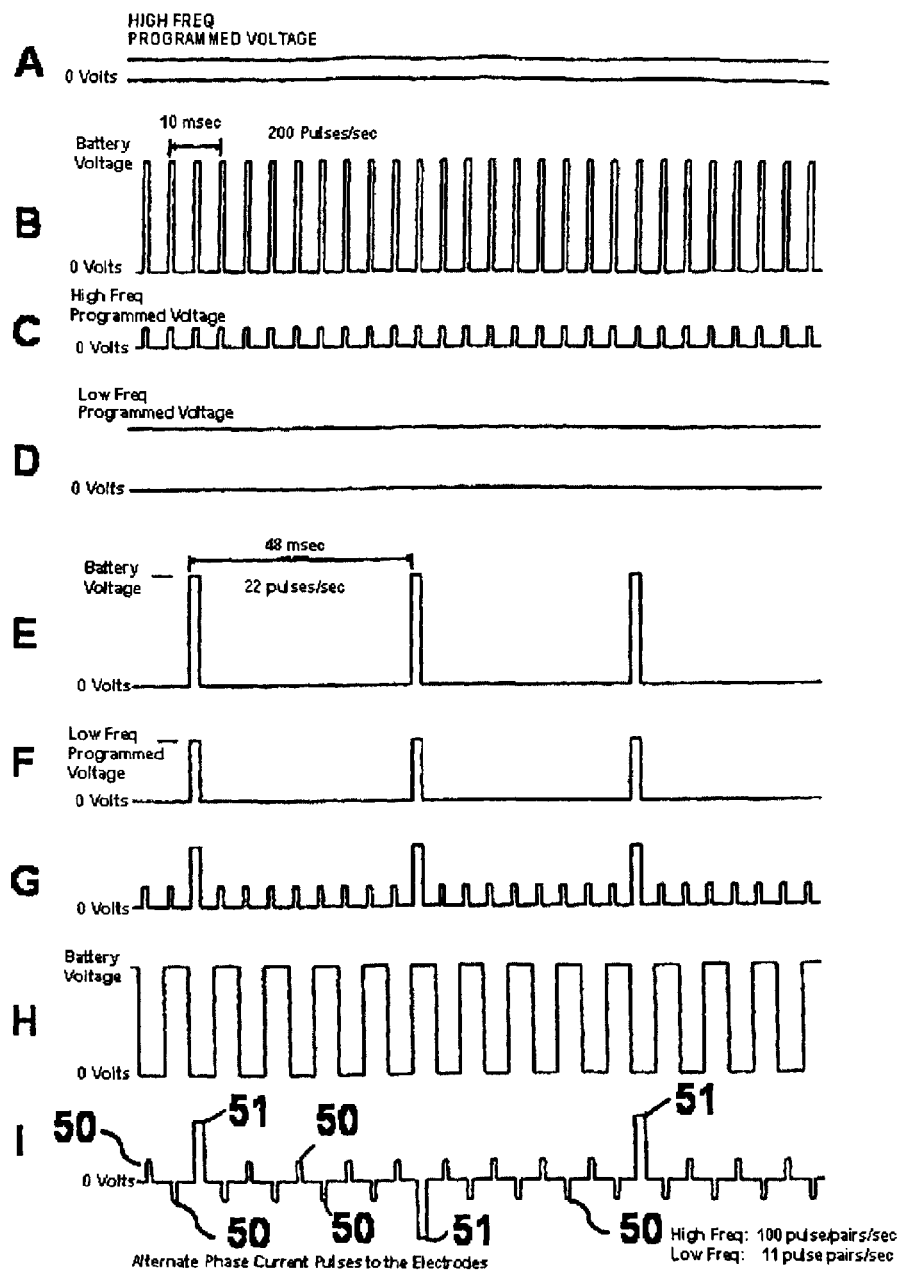
FIG. 8 illustrates a wave form for controlling a bladder in accordance with the present invention.

During the programming process the high frequency amplitude and the low frequency amplitude information can be stored as digital information in their respective RAM (read only memory) data storage 24, 25. Digital-to-analog converters 30, 31 convert the digital data into a constant voltage that is sent to their respective analog gates 32, 33. These constant voltages are gated into a high frequency and low frequency mixer 40. The gate control comes from the respective high frequency and low frequency pulse generators 41, 42. The pulse generators preferably operate at frequencies that are two times the frequency of the desired out put pulse pairs. Micro-controller 23 provides the signals that turn the pulse generators on and off. As described previously, the high frequency pulses are turned on to increase the bladder capacity and to relax the urethra sphincter. The low frequency pulses are turned on when bladder voiding is required. A voltage to current converter 43 converts the string of voltage pulses of the combined high and low frequency pulses into constant current pulses. The direction of every other pulse in the pulse train that comes from the voltage to current converter is reversed by pulse phase reversing switches 44. This produces the "alternate phase" pulses that are sent to the sacral nerves via the electrodes and leads that are attached to the implant. A square wave voltage from the micro-controller controls the reversing switches. The resulting wave form is shown in FIG. 8. The high frequency, low amplitude, alternate phases are identified as 50 while the low frequency, high amplitude, alternate phases are identified as 51.

In certain embodiments, the electromagnetic detector 20 can comprise a standard implantable antenna coil adapted to receive the "rf" signal(s) transmitted from the controller 21. Such receivers are well known to those of skill in the art. In certain instances, for example, the receiver can be similar to the type manufactured by Avery Laboratories, Inc. under Model No. 1-110 (bipolar).

The illustrated pulse generator comprises a pressure sensitive switch that can be activated at will by the operator (patient, attendant, physician, etc.). Typically the switch is activated by palpitation by the operator. In various embodiments, activation/control can be effected by use of the controller 21 without recourse to the pressure sensitive switch.

While the generator is illustrated with four leads to electrodes, generators that can drive more (e.g. 8, 10, 12, 16 leads, etc.) or fewer leads are also contemplated. In certain embodiments, the pulse generators allow independent control of essentially all signal parameters. Thus, pulse pair frequency, delay between pulses comprising a pair, amplitude of each pulse within a pulse pair, and pulse width of each pulse comprising a pulse pair can be independently controlled. In addition, pulse generators can readily be fabricated that deliver different signals to different electrode leads The implantable pulse generator is typically encased and sealed in a biocompatible material (e.g. silastic, ceramic, etc.).

In certain embodiments, various functions embodied by the illustrated implantable pulse generator can be effected by an external pulse generator. Indeed, in certain embodiments, the implanted components can comprise little more than one or more antennal coils connected to appropriate electrodes and all pulse generation functions can be regulated by an external or pericutaneous pulse generator. In this regard, it is noted that U.S. Pat. No. 6,366,815 describes an implantable stimulator electrode for stimulation of nerves adapted to be surgically implanted around a nerve bundle. The stimulator comprises one or more electrode means which, when implanted around the nerve bundle, surrounds the nerve bundle totally or partly. The electrode and associated electronic circuit are coupled to and powered by one or more receiving coils. The electrode, when implanted, acts as a remote addressable maintenance free unit that is powered telemetrically.

In certain embodiments, an external pulse generator can be used to supplement an internal implantable pulse generator. The external generator can then be used to optimize stimulus signals for the particular electrode configuration and/or patient physiology. Once an optimal signal program is determined, this program can then be downloaded to and stored by the implanted pulse generator.

In certain embodiments, the use of an implant that utilizes an external device that sends a voiding code to the implant via an electromagnetic coupling is contemplated. Also contemplated are implants that do not include batteries in the implant. Power to operate such implant(s) can be provided by an external device that is located on the outside of the body opposite the implant. The implant is programmed by the external device, and the voiding period is preferably initiated by pressing a button on the external device. Illustrative circuits that can be used in the devices of this invention or that can be modified for use in the methods described herein are illustrated, e.g., in FIG. 22.

The pulse generator is typically connected to electrode leads for transmitting the electrical pulse(s) to the nerves or nerve roots. Typically a connector is used for coupling the implantable pulse generator to the electrode leads. This permits surgical implantation of the electrodes and then subsequent coupling of the electrodes to the pulse generator. Suitable connectors are well known to those of skill in the art (see, e.g., U.S. Pat. Nos. 6,366,820 and 6,327,502).

B) Electrodes.

The electrodes can be fabricated of any of a variety of biocompatible, non-toxic conducting materials commonly utilized as implantable electrodes. Such materials are well know to those of skill in the art and include, but are not limited to iridium, titanium, titanium alloy (e.g. TiN, titanium dioxide), platinum, platinum alloy, gold, gold alloy, and the like (see, e.g., U.S. Pat. Nos. 5,181,526; 5,074,313; 4,352,360; 5,931,862 ; 5,755,762; 5,824,016; 3,749,101; 5,628,778; and 4,502,492).

The electrodes can be of a variety of shapes and sizes. Such shapes include, but are not limited to example, ribbons, buttons, pads, collars, etc. The electrodes can be malleable and shaped for metal for partially or completely surrounding the nerve or nerve root or the electrodes can have tapered shape like a needle.

FIG. 5 illustrates an example of placement of the electrodes and pulse generator inside a patient. Preferably, there are multiple electrodes, one or more for each nerve root. After the electrodes are placed around appropriate sacral roots 12, leads 13 are brought around to the implantation site of the pulse generator. The leads are preferably attached to the pulse generator via mating connectors on the leads and the pulse generator.

The electrodes can be applied to any nerve including roots such as the sacral root and peripheral nerves such as the sciatic nerve. Contact can be anywhere along the nerves including intradurally and extradurally.

In various embodiments, the electrodes are monopolar, bipolar, tripolar, or quadrapolar, or various combinations thereof.

Figure 9:
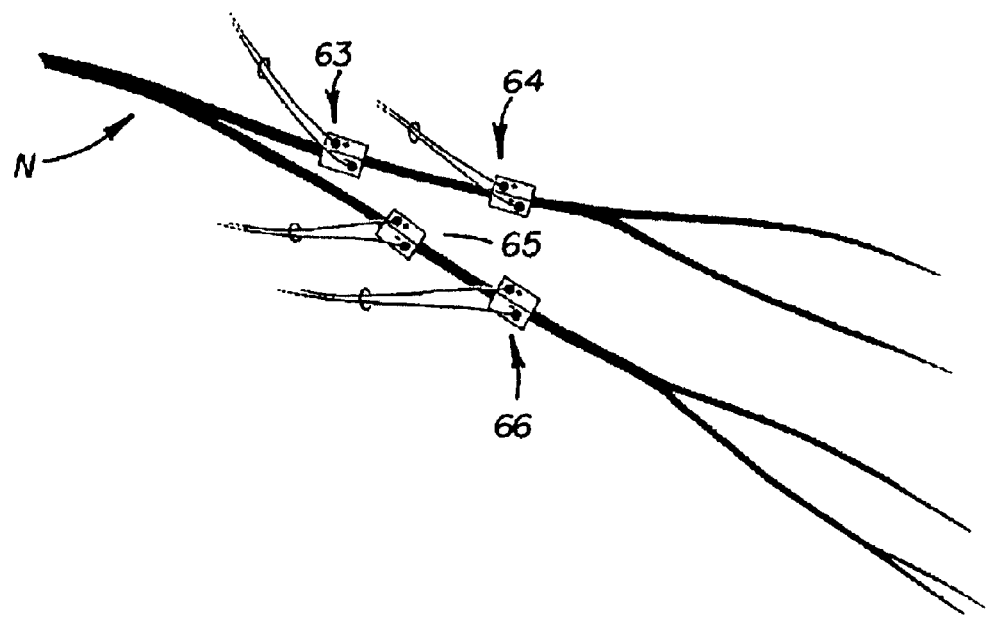
FIG. 9 illustrates the connection of electrodes to various nerve bundles. A multiplicity of electrode pairs 63, 65, and 66 are attached to separate nerve bundles, and multiple electrodes 63 and 64 are attached to the same nerve bundle.

FIG. 9, illustrates the connection of electrodes to various nerve bundles. This figure illustrates a multiplicity of electrode pairs 63, 64, 65, and 66 are attached to separate nerve bundles. In various embodiments, each pair of electrodes can be activated independently or all together to insure effective stimulation of the nerve.

Figure 10:
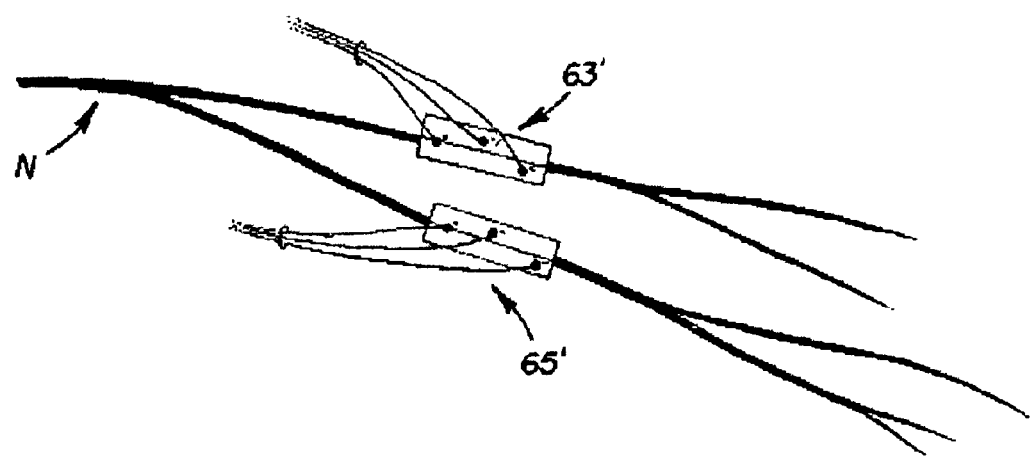
FIG. 10 illustrates a multiplicity of active electrode contacts employed on a single nerve.

FIG. 10 illustrates another embodiment where a multiplicity of active electrode contacts are employed on a single electrode.

It is noted that because the methods of this invention provide differential activation/inhibition of small or large fibers based simply on the stimulus signal, unlike nerve stimulation electrodes previously known, the electrodes used in this invention need not be contacted predominantly to different fiber types. Rather, the electrodes of this invention are conveniently connected to a mixed nerve fiber or a nerve root.

The embodiments described above are meant to be illustrative and not limiting. Other methods of contacting nerves or nerve roots with electrodes are known to those of skill in the art and can be routinely implemented.

C) Inteprated control system.

In certain embodiments, this invention contemplates integrated control systems for control of bladder or other internal organs. Such control systems typically comprise an electrical pulse generator configured to produce an alternate phase high frequency, low amplitude pulse and an alternate phase low frequency, high amplitude pulse to one or more a sacral nerve(s) or nerve root(s), and at least one electrode and more typically a plurality of electrodes that can be coupled to a nerve and transmit an electrical signal from the pulse generator to the nerve root(s).

The system can further comprise a means for actuating and/or for programming the pulse. Such means can comprise a controller (e.g. an rf controller, a magnetic controller, an induction controller, etc.). In certain embodiments, the system comprises a pressure sensitive switch coupled to or on the electrical pulse generator that permits mechanical activation of the device.

In various embodiments, the system comprises a plurality of electrodes (e.g. at least two electrodes, preferably at least 4 electrodes, in certain embodiments, at least 6 or 8 electrodes and in certain other embodiments, at least 10 or 16 electrodes) that can be coupled to one or more pulse generators, e.g. through an electrode connector.

The system can comprise an internal power source (e.g. a battery) as a component of the pulse generator or separate from the pulse generator, e.g. an implantable battery pack or an external battery pack. In certain embodiment, the system comprises an external power source that can transmit power to the internal pulse generator and/or to the internal electrode(s).

V. Surgical Procedures for Inserting Device to Control Bladder Evacuation

U.S. Pat. No. 4,607,639 describes various surgical procedures for insertion of a pulse generator and associated electrodes for controlling bladder function and/or the function of other internal organs. The devices of this invention can be surgically inserted in a similar manner.

FIG. 3 illustrates an operative procedure whereby continence and evacuation of bladder B is closely controlled in a particular patient, such as a quadriplegic using devices according to this invention. It is noted that many of the procedures described in U.S. Pat. No. 4,607,639 contemplate sectioning of the superior somatic nerve Ss to eliminate activation of the external sphincter. The methods of this invention are particularly advantageous in obviating the necessity for sectioning the superior somatic nerve because of the independent inhibition of small and large fibers in a mixed fiber nerve. Thus, in the methods described herein, such sectioning is optional and preferably omitted.

Similarly, using the methods of this invention it is also unnecessary to do selective sectioning of motor roots. Using the stimulation patterns described herein, simple application of the electrode to the nerve root permits independent inhibition/activation of small and large fibers in a mixed fiber nerve. Thus, if desired, the sectioning of nerve roots described herein can be omitted.

The particular operative procedure utilized will depend upon a particular patient's ability to respond to electrical stimuli at strategic locations on his or her nervous system in the pelvic plexus region. For example, it is assumed in operative procedure illustrated in FIG. 3 that the patient is unable to self-control his or her bladder functions and that such locations have been evaluated pre-operatively.

Figure 13:
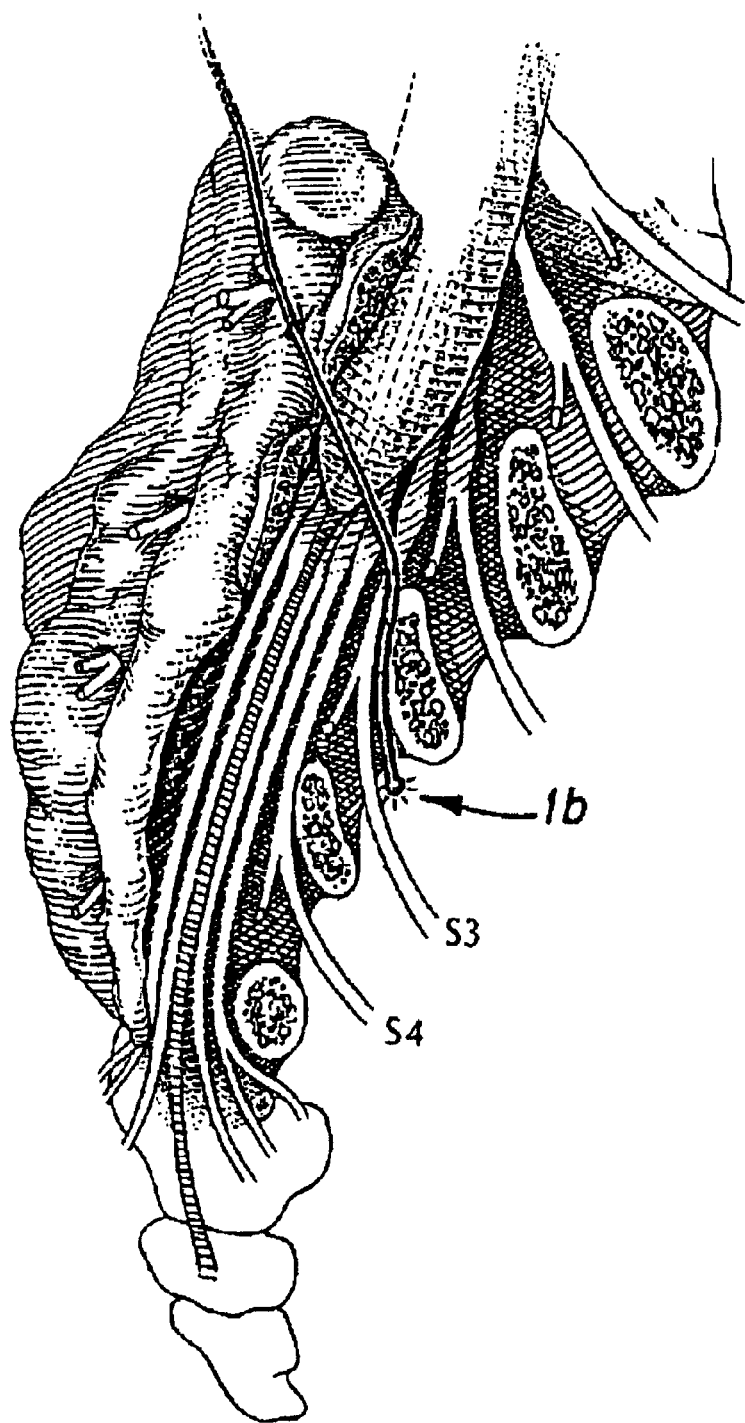
FIG. 13 schematically illustrates the percutaneous implantation of an electrode adjacent to the S3 sacral roots through the dorsum for the purpose of selectively stimulating such nerve.

As illustrated in FIG. 3, after the anatomical location of the S3 sacral nerve is identified, such as by the percutaneous insertion and electrical energization of an electrode placed at least in close proximity to such nerve, as illustrated in FIG. 13, the dorsal (sensory) root D and ventral (motor) root V can be surgically separated bilaterally on each side of sacral segment S3 although such separation is not necessary. An electrode 2 can then be attached, e.g. by sutures and implanted on each ventral root V for purposes of external excitation and stimulation, with the device(s) described herein.

In previous practice, after bilateral implantation of electrodes 2 on ventral components or roots V, each superior somatic nerve Ss is often sectioned bilaterally, e.g., at 3 to eliminate any increase in the resistance normally provided by the levator ani muscles at least partially surrounding external sphincter E and controlled by superior somatic nerve Ss. However, using the devices of the present invention, selective inhibition of the somatic fibers can be achieved (using high frequency small amplitude pulse pairs as described above) and consequently sectioning of the superior somatic nerve Ss can be avoided.

Superior somatic innervation Ss is commonly described in anatomy books (e.g., CIBA or Gray's) as part of the innervation to the levator ani muscles, whereas inferior somatic innervation SI is classically described as the pudendal nerve in Alcock's Canal. It should be noted that an internal sphincter I will normally open when the bladder contracts and thus requires no artificial control.

The operative procedure illustrated in FIG. 3 is generally preceded by identification of the S3 sacral nerve and confirmation that it controls bladder and related functions by use of intraoperative stimulation and urodynamic recordings. Conditions sufficient to effect bladder evacuation without sacrificing continence, i.e., the ability to retain contents of the bladder until conditions are proper for urination, are assumed to be confirmed.

Pre-operative electrostimulation can be achieved by the use of a monopolar or bipolar probe for stimulating the various nerve bundles. A nerve stimulator can be used to deliver a DC square wave (or other stimulus) for stimulation purposes. Suitable nerve stimulators are known to those of skill in the art. For example, in certain embodiments, the nerve stimulator can be of the type manufactured by Grass medical instruments of Quincy, Mass., under Model No. S-44.

Suitable electrodes and electrode materials will be known to those of ordinary skill in the art. For example, the electrodes can be of the type disclosed in U.S. patent application Ser. No. 597,502. In certain embodiments, each electrode can constitute a bipolar cuff electrode having an inside diameter approximating, e.g., 3–5 mm and provided with, e.g., 1 mm by 2 mm platinum contacts having a 3 mm separation placed opposite each other about the periphery of ventral nerve root V. This type of electrode is manufactured by Avery Laboratories, Inc. under Model No. 390.

Figure 11:
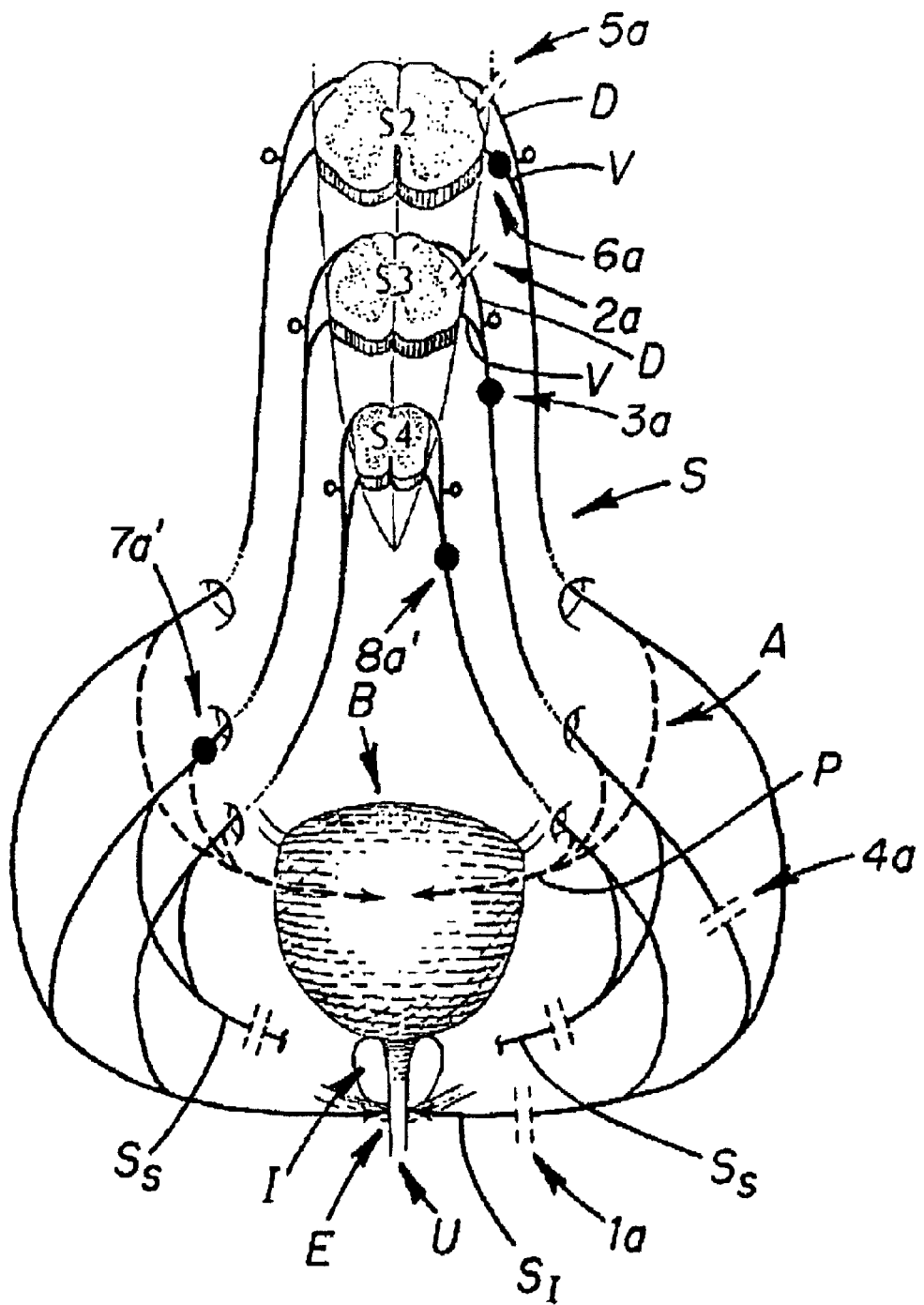
FIG. 11 and FIG. 12 are views similar to FIG. 3, but illustrate additional operative procedures for controlling bladder evacuation and related functions.

A) Alternative procedure for controlling bladder evacuation (FIG. 11).

FIG. 11 illustrates optional variations to the operative procedure illustrated in FIG. 3 which can potentially enhance bladder evacuation. After the various critical nerves for controlling bladder evacuation have been identified by intraoperative stimulation and urodynamic recordings, each of the S2, S3 and S4 sacral nerves are separated to isolate the respective ventral and dorsal roots thereof. Pudendal or inferior somatic nerve S1 is then sectioned unilaterally to isolate external sphincter E on one side. Dorsal root D of the S3 sacral nerve can be sectioned at 2a to isolate the sensory function thereof. Although illustrated as being performed unilaterally, and as stated above, in certain applications it may prove desirable to perform such sectioning bilaterally.

An electrode 3a can be implanted on the entire S3 sacral nerve unilaterally, with or without dorsal rhizotomies at other sacral levels. The S3 sacral nerve can then sectioned at 4a unilaterally (or bilaterally), downstream of pelvic nerve P to isolate this nerve's contribution to inferior somatic nerve SI. It should be noted that electrode 3a is thus positioned on the S3 sacral nerve to stimulate the detrusor muscles of bladder B, via pelvic nerve P.

After appropriate separation of the dorsal and ventral roots of the S2 sacral nerve, the dorsal root is sectioned at 5a unilaterally (or bilaterally) and an electrode 6a is suitably implanted on the ventral root V of the S2 sacral nerve. While superior somatic nerve Ss can be sectioned bilaterally, as described above in reference to the FIG. 3 operative procedure, to eliminate any additional increase in resistance from contraction of the levator ani muscle when the bladder is contracting for evacuation purposes, utilization of the devices of this invention typically obviates the need for such sectioning.

The above options will also tend to eliminate or minimize a response in the pelvic floor sphincter which could otherwise prevent low resistance voiding of the bladder synchronous with stimulation. These optional variations address the possibility that excessive residual sphincter activity remains with stimulation after the operative procedure has been attempted. Sphincter response may be reflexively produced which suggests the need for dorsal sectioning at 2a and 5a in FIG. 11, or directly produced to suggest sectioning 1a of inferior somatic SI, unilaterally or bilaterally. The above steps must, of course, be carefully evaluated prior to the selected operative procedure so as not to compromise continence or the contraction of the bladder or bowel or nerves controlling the erection process.

Additional optional procedures may include percutaneous implantation of an electrode 7a' on sacral nerve S3 and/or S4, upstream of the point whereat the autonomic nerve roots forming pelvic nerve P separate from the respective sacral nerve proper, to aid in bladder contraction through the pelvic nerve. A further option contemplates implantation of a cuff electrode 8a' around sacral nerve S4, either unilaterally as shown or bilaterally, to assist in the control of bladder evacuation. It should be understood that above sectioning steps 2a and 5a, as well as the implantation of electrodes 3a, 6a and 8a', can require laminectomy, i.e., incision of the posterior arch of the vertebrae.

Figure 12:
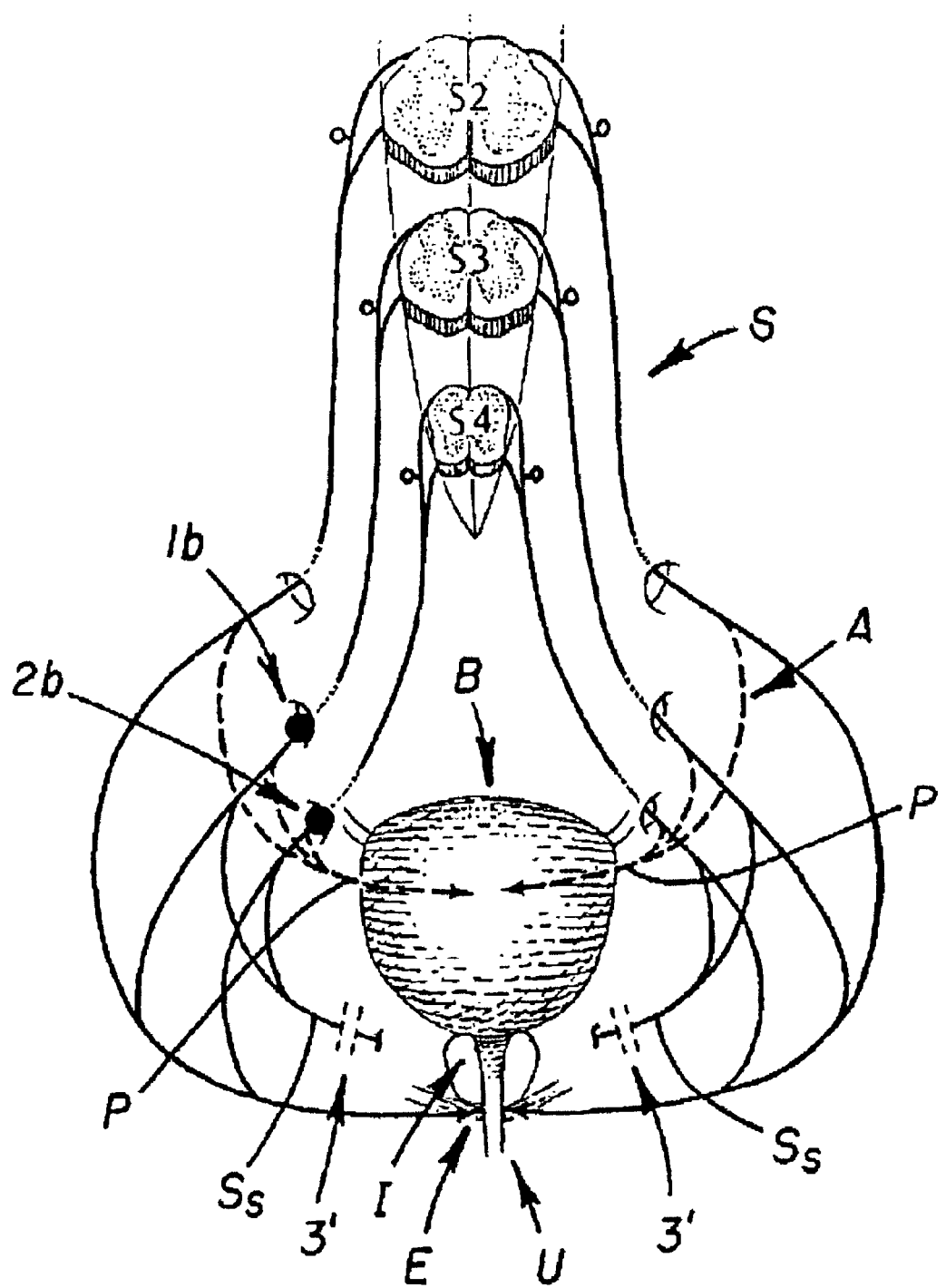

B) Non-laminectomy procedure for controlling visceral organs (FIGS. 12 and 13).

FIG. 12 illustrates an operative procedure in which an electrode 1b is implanted onto the S3 sacral nerve through a sacral foramen without excising the posterior arch of the vertebrae. A second electrode 2b can be implanted in a like manner on the S4 sacral nerve, either in addition to or in lieu of electrode 1b. These electrode implants can be effected unilaterally, as illustrated, or bilaterally, depending on the pre-operative test results. Although not required with the devices of this invention, superior somatic nerve Ss can, optionally, be sectioned at 3', either unilaterally or bilaterally as illustrated in FIG. 12.

This operative procedure will normally provide means for selectively eliminating or suppressing spastic detrusor activity, spastic urethral and pelvic floor activity and spastic anal sphincter. Such an approach can further suppress or enhance erection.

FIG. 13 illustrates the percutaneous implantation of electrode 1b through the dorsum and the sacral foramen of sacral segment S3 for the purpose of selectively stimulating the S3 sacral nerve. After the appropriate depth and location of the S3 nerve has been verified by electrostimulation and recorded urodynamically, electrode 1b can be inserted through the hollow spinal needle used for such stimulation with the wire lead connected to the electrode being suitably sutured in place, as shown, for attachment to a receiver (not shown), as will be described more fully hereinafter. This percutaneous method can also be used to temporarily implant an electrode on any one or more of the sacral nerves for testing purposes, i.e., to record activity in the bladder in response to stimulation of one or more of the nerves by the electrodes to thus determine which nerve or nerves are controlling the bladder functions. This procedure can be conducted unilaterally or bilaterally.

For example, electrode 1b can be percutaneously placed on the S3 sacral nerve with the external extremity of the wire attached to the electrode then being taped to the skin, along with a receiver connected thereto. The patient could then resume his day-to-day lifestyle and be allowed to stimulate the nerve or nerves artificially via a transmitter compatible with the receiver. If the response is positive and complete relief is achieved, the electrode or electrodes could be permanently implanted or temporarily implanted for the purpose of correcting any dysfunction by "retraining" the nerve and associated muscles. Should little or no improvement result, the same procedure could be followed to accurately ascertain which nerve or nerves require stimulation. Thus, this invention contemplates not only the implantation of one or more electrodes in the sacral nervous system for controlling evacuation of a visceral organ or the like, but also contemplates use of such electrodes and procedures to rehabilitate muscle dysfunction by neuromodulation of muscular behavior.

C) Additional optional operative procedures (FIGS. 14–18).

Figure 14:
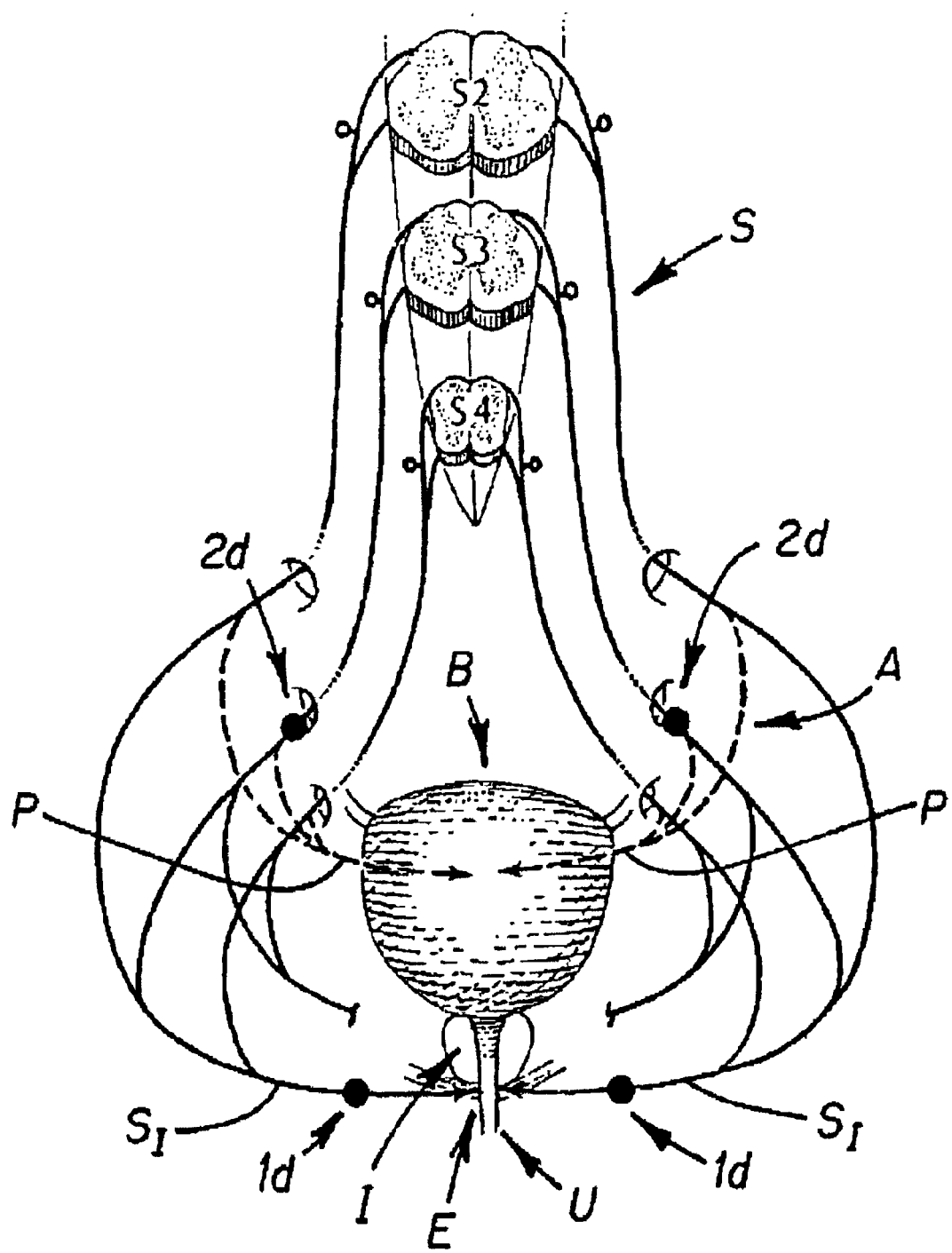
FIGS. 14, 15, 16, 17, and 18 are views similar to FIG. 3, but illustrate additional operative procedures for controlling bladder evacuation and related functions.
Figure 15:
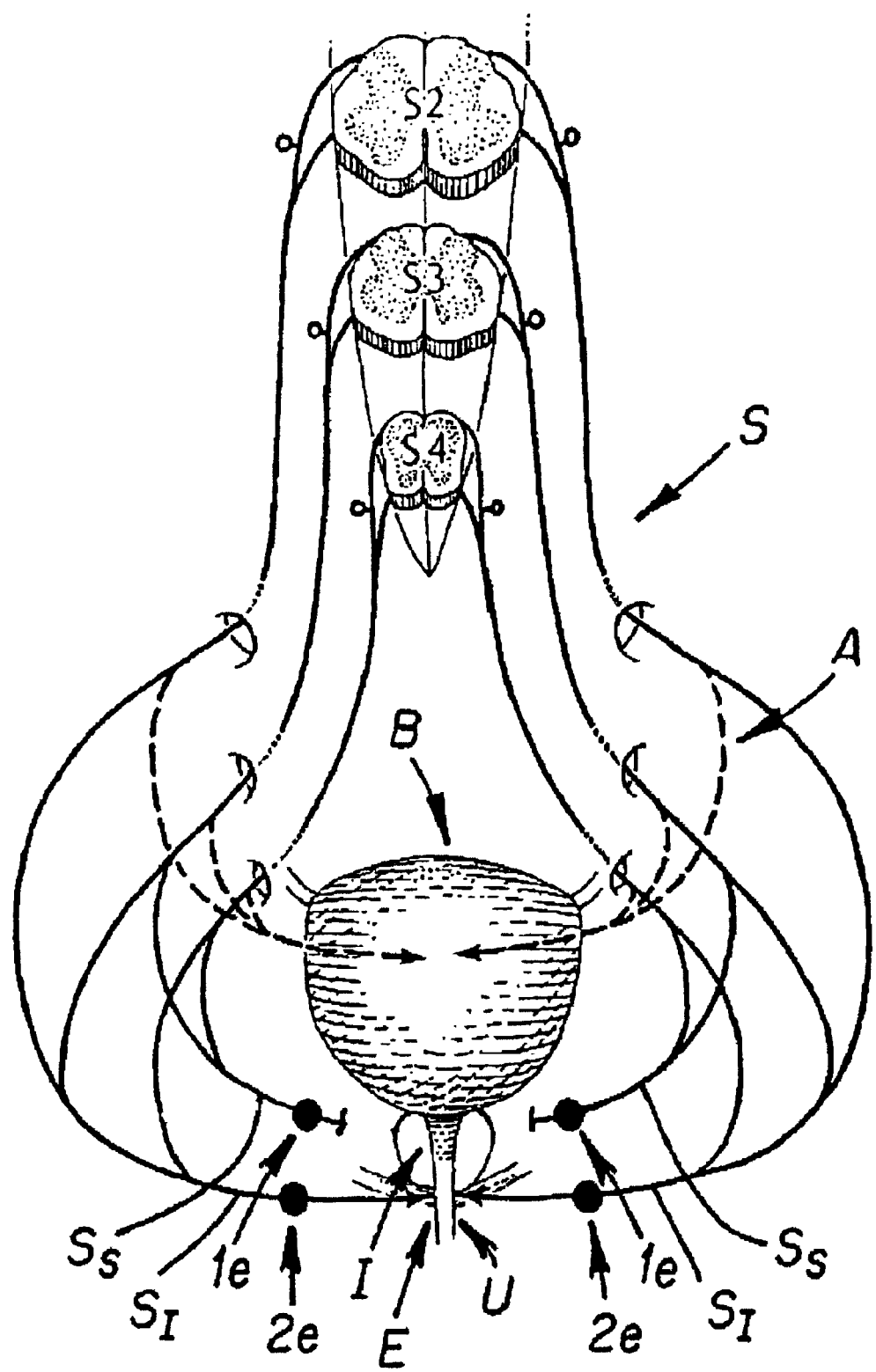

In another procedure, illustrated in FIG. 14, electrodes 1d are implanted bilaterally on inferior somatic nerve SI and electrodes 2d are implanted bilaterally on the S3 sacral nerve percutaneously. As illustrated in FIG. 15, electrodes 1e can be implanted bilaterally on superior somatic nerve Ss and electrodes 2e are implanted bilaterally on inferior somatic nerve SI.

Figure 16:
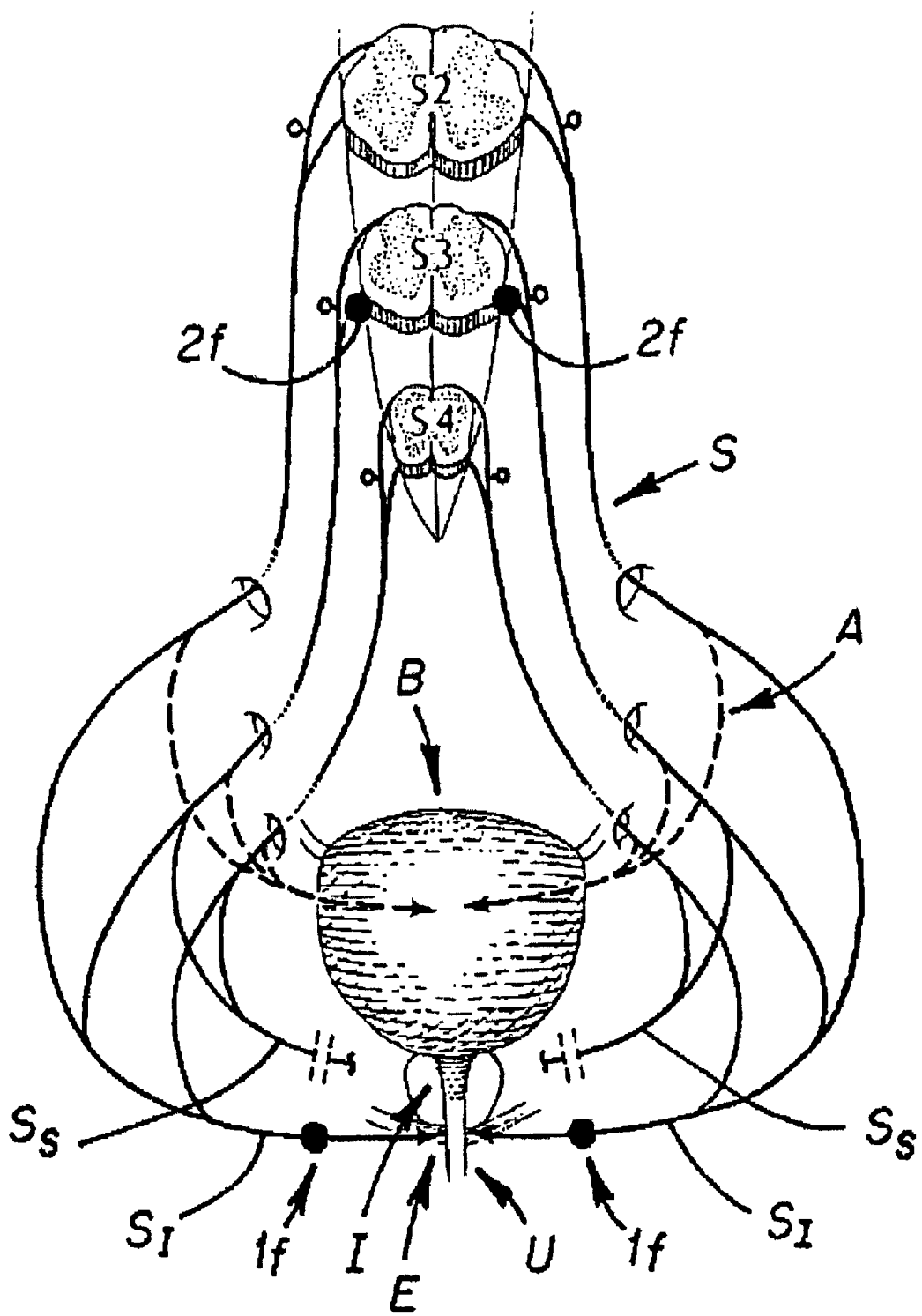

FIG. 16 illustrates another operative procedure for controlling continence and bladder contraction. In the illustrated operative procedure, electrodes 1f are implanted bilaterally on inferior somatic nerve S1. Superior somatic Ss is, optionally, sectioned bilaterally, as illustrated, and a pair of second electrodes 2f can be implanted bilaterally on the separated ventral root V of the S3 sacral nerve.

Figure 17:
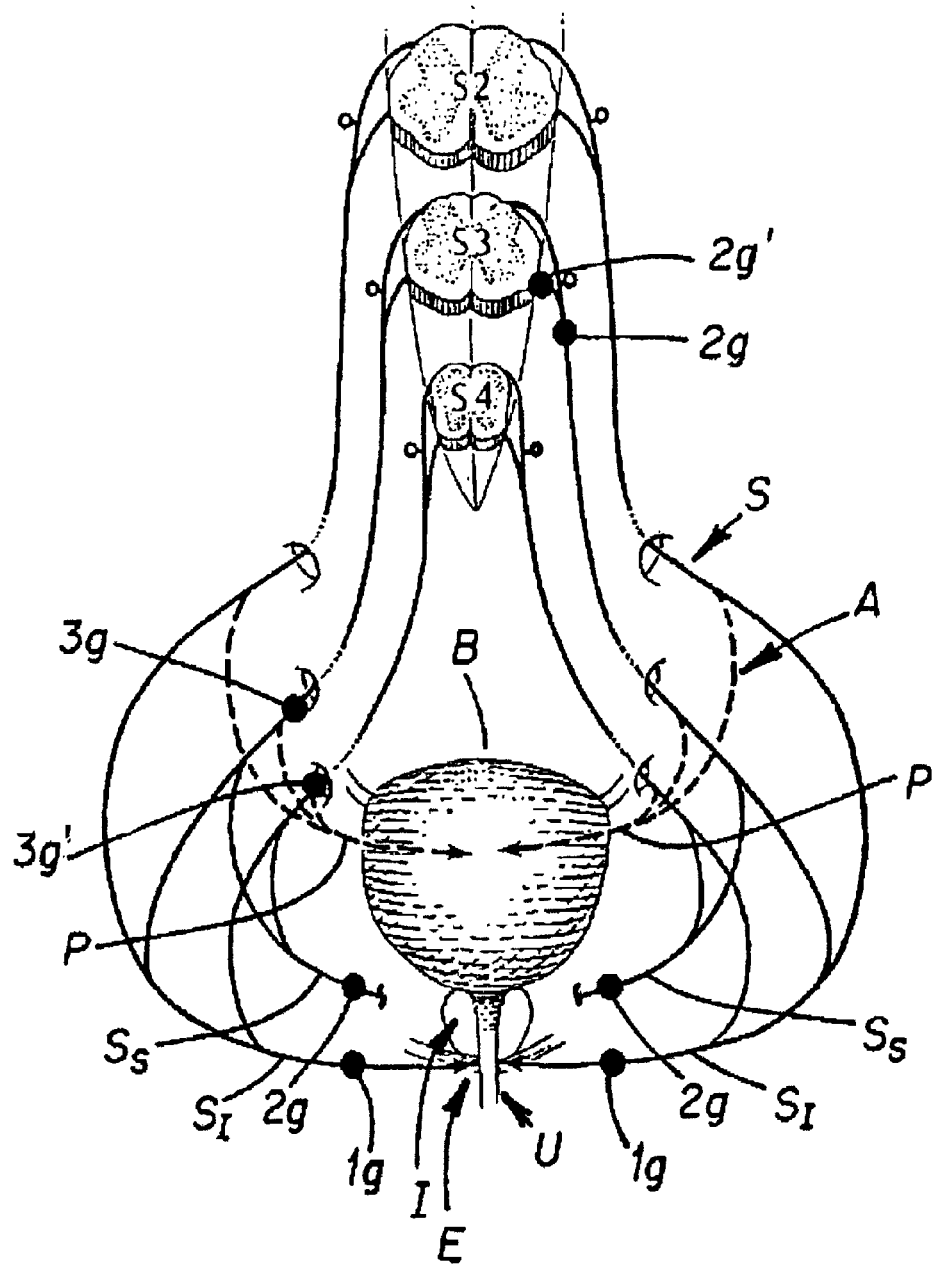

FIG. 17 illustrates an operative procedure particularly adapted for achieving continence due to muscle weakness of the bladder or bowel. Electrodes 1g and 2g are implanted bilaterally on inferior somatic nerve SI and on the S3 sacral nerve, as illustrated. As an option to implantation of the electrode unilaterally on the S3 sacral nerve, an electrode 2g' could be implanted on the ventral root thereof. In addition, an electrode 3g is implanted unilaterally on the S3 sacral nerve percutaneously. Alternatively, an electrode 3g' could be implanted on the S4 sacral nerve, also percutaneously.

As another option, illustrated in FIG. 17, another electrode 2g could be implanted on superior somatic nerve Ss, either unilaterally or bilaterally, as illustrated. The FIG. 17 operative procedure illustrates the two components of sphincter contraction with the number of implants and their locations being dependent on recruitability of muscle activity in individual patients and/or the ability of percutaneous technique to adequately couple the electrodes with the appropriate nerve fibers.

Figure 18:
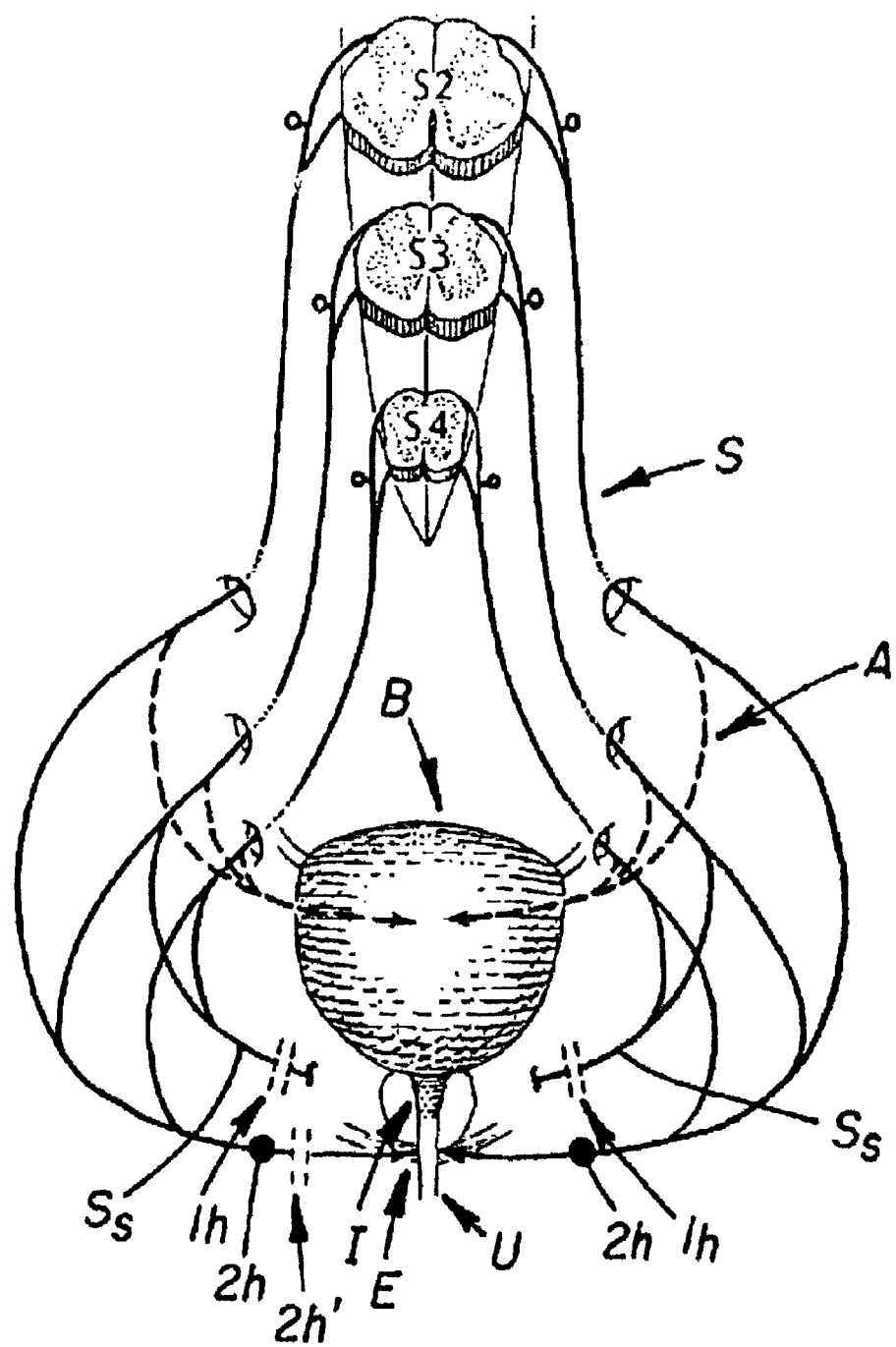

FIG. 18 illustrates an operative procedure particularly adapted for controlling autonomic dysreflexia and bladder storage. Electrodes 2h are implanted on the inferior somatic nerve bilaterally. Although not required with the devices of this invention, superior somatic nerve Ss can be sectioned bilaterally at 1h. Alternatively electrode 2h could be implanted unilaterally with the opposite side of the inferior somatic nerve being sectioned at 2h'.

The operative procedures illustrated in FIGS. 3, and 11–18 are examples of specific procedures applicable to particular patients. These examples are intended to be illustrative and not limiting. The various steps described above in connection with one particular procedure could he included with or substituted in lieu of steps included in one or more of the other procedures to meet a particular case study. For example, many of the above steps could be performed bilaterally where disclosed unilaterally, and vice versa.

In addition, other suitable surgical procedures for implantation of electrodes and/or pulse generators will be known to those of skill in the art.

It follows when reciting the method steps of "implanting" or "attaching" an electrode to a particular nerve or "sectioning" a particular nerve, etc., intend to cover both unilateral and bilateral procedures.

Various combinations of operative procedures are described herein for effecting the desired neurostimulation for specific case studies (male or female). For example, a quadriplegic who has suffered a neck injury that damages the spinal cord will normally require an operative procedure wherein control of bladder B and external sphincter E are of utmost importance. In addition, the quadriplegic will suffer uncontrolled bowel evacuation, for example, which is concurrently controlled when bladder control is effected by such operative procedure. In addition, it may prove desirable to modulate other voiding dysfunctions that may occur as a result of one or more of a multitude of other neurological reasons.

Selection of the various options described herein would typically be based upon evaluation of responses obtained from preoperative stimulation recorded urodynamically. The ability of a particular procedure to be conducted percutaneously or surgically, or a combination thereof, further expands application of this invention. Those skilled in the medical arts relating hereto will also appreciate that the above operative procedures can be utilized to control not only bladder functions but also functions of other organs, such as the colon, bowel, anal sphincter, etc.

Thus, it is emphasized that the specific operative procedures herein described can be combined with one or more of the other procedures described herein or otherwise known to those of skill in the art, as dictated, e.g., by pre-operative evaluation of responses to stimulation recorded urodynamically. For example, when a particular procedure (e.g., electrode implant, nerve separation, sectioning, etc.) is described as being performed bilaterally, clinical testing may indicate that in certain other patients, a unilateral procedure is necessary (and vice versa). Likewise, the specific steps or procedures utilized in one operative procedure (e.g. FIGS. 3, and 11–18) may be utilized in combination with one or more steps utilized in other operative procedures, as will be appreciated by those skilled in the arts relating hereto.

VI. Kits

In various embodiments, this invention contemplates kits for the practice of the methods described herein. Typical kits comprise a container containing one or more electrodes and/or one or more pulse generators, and/or one or more pulse generator controllers as described herein. In certain embodiments, the electrode(s) and/or the pulse generator are packaged in sterile packaging or in packaging that can be sterilized (e.g. autoclaved).

In addition, the kits optionally include labeling and/or instructional materials providing directions for the surgical implantation of electrodes and/or the pulse generator(s) described herein, and/or for activating or programming the pulse generators, for optimizing electrical signals to provide a particular response, and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Means and Device for Selective Activation of Small Fibers in a Mixed Nerve

The purpose of this experiment was to investigate the use of electrical stimuli to selectively stimulate small diameter fibers to the exclusion of stimulating the larger fibers. The general idea was to use high frequency sinusoidal current or voltage to disable the larger fibers, thus producing flaccid paralysis of the skeletal sphincter muscles. Then the application of low frequency sinusoidal current or voltage excites the small diameter fibers that contract the detrusor muscles.

The sinusoidal wave form, while effective in blocking the generation of the impulse in nerve fibers was not an efficient form of energy. Since energy (power) must be conserved when an implantable stimulating device is powered by a battery, the most efficient form of stimulus energy is important.

A device was designed and built that allowed comparison of the effects of the sinusoidal wave with an alternated phase rectangular wave. With this device, the sinusoidal wave could be gradually changed into alternate phase rectangular pulses. Surprisingly, the latter proved to be as effective in blocking the initialization and transmission of impulses.

Bladder voiding was accomplished by applying the high frequency alternate current to one bipolar electrode placed on a sacral root and applying a low frequency alternate phase current to another bipolar electrode placed on the same root. The low frequency pulse generator was turned on after the high frequency pulse generator produced sphincter fatigue. The resulting bladder pressure produced voiding.

In another experiment, an electrode was used that had three contacts. One stimulus generator was connected to one pair of adjacent contacts and the other stimulus generator was connected to the other pair of adjacent contacts with the center contact common to both generators. This change was as effective as using two separate bipolar electrodes, but now the total length of the electrode attached to the root was shorter. The shorter the electrode that is placed around a nerve the lower the risk of trauma or damage to the nerve.

Figure 19:
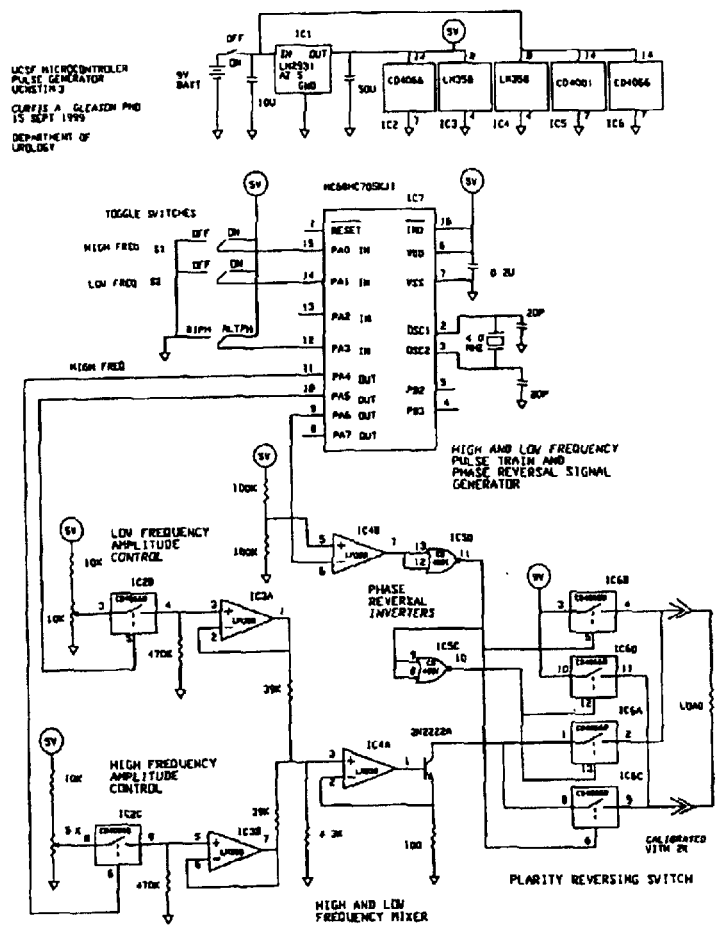
FIG. 19 illustrates one embodiment of a pulse generator suitable for practice of the methods of this invention.
Figure 19:
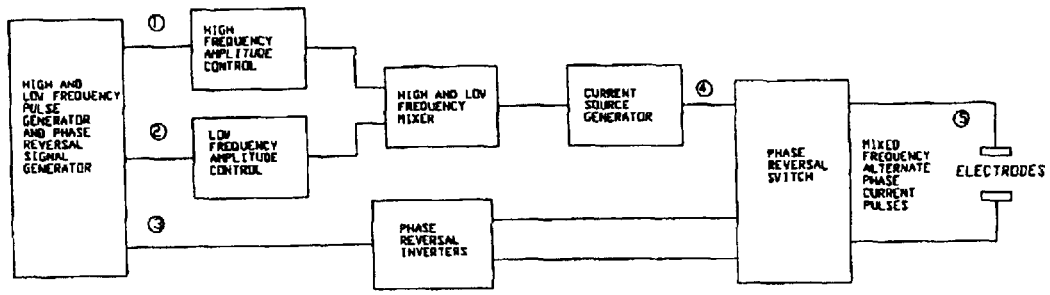

We built a device that combines the high and low frequency biphasic stimulus wave forms and applies the mixed pattern to a single electrode pair (see, FIG. 19). Each wave form had a separate amplitude control so that the proper amplitude of each stimulus could be applied to the nerve. Upon receiving a start signal, the device generates a train of high frequency biphasic current or voltage pulses. After a time, for example, of up to about 15 seconds, to be certain that the sphincter was flaccidly paralyzed, a train of low frequency alternate phase current or voltage pulses were superimposed on the high frequency pulses to produce a combined pulse pattern. The combined pulse pattern could be stopped either manually or automatically after a preset on period. The single electrode pair permitted the shortest electrode possible to enclose the nerve, thus imparting the least amount of trauma to the nerve. This device was tested and shown to be effective in producing voiding in the acute canine model.

The device could be used in any situation that requires the flaccid paralysis of skeletal muscles and the excitation of smaller fibers in a mixed nerve.

Figure 20:
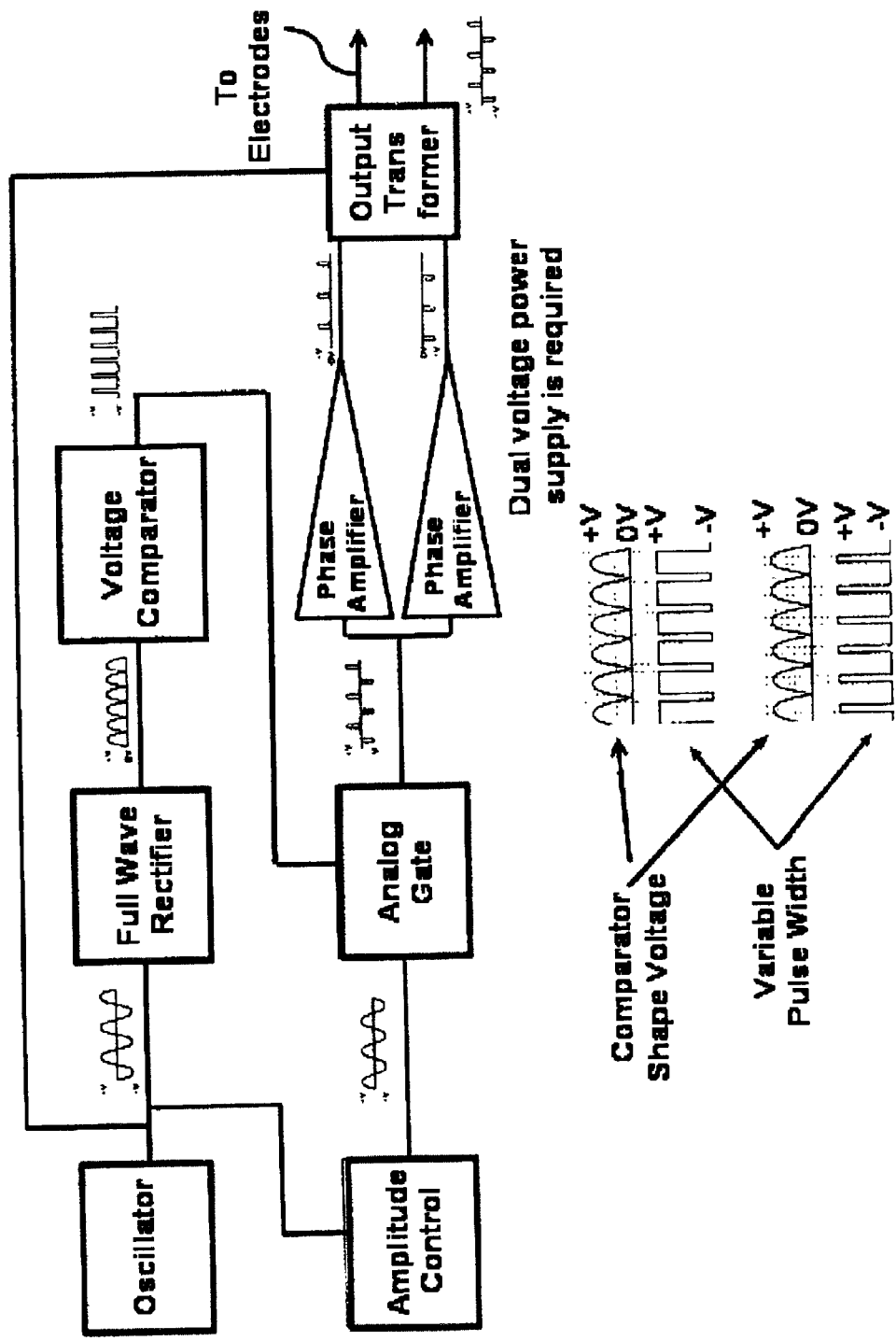
FIG. 20 illustrates one embodiment of a pulse generator suitable for practice of the methods of this invention.
Figure 21:
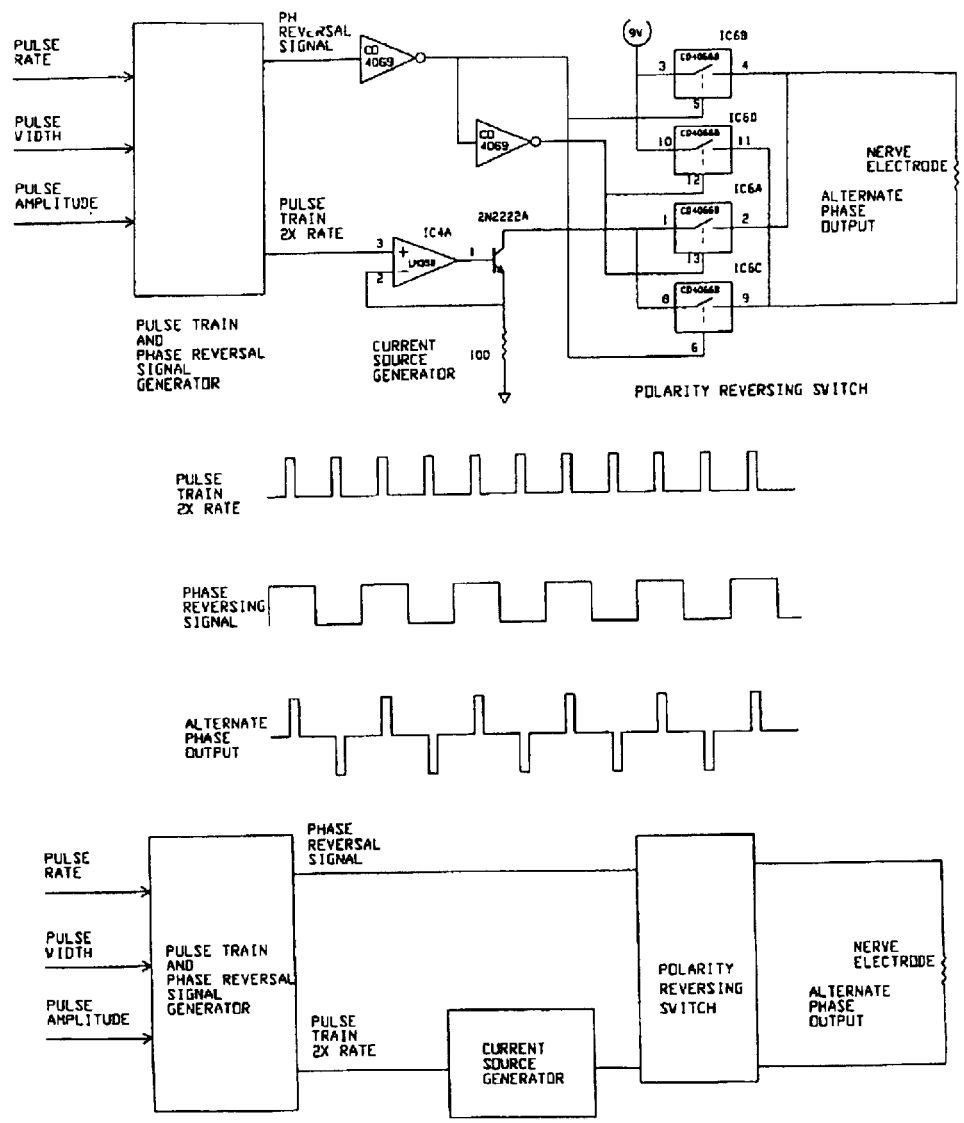
FIG. 21 illustrates shows a circuit, wave form, and a block diagram of a device that can produce the alternate phase pulses using a single voltage source without an output transformer.

The described device can generate a low frequency wave form (20 biphasic pulses per second or 20 alternate phase pulses per second), a high frequency (100 biphasic pulses per second) or the combination of the high frequency and low frequency pulses (see, e.g. FIGS. 20 and 21). In a simplified embodiment, the implantable stimulator could have only one version of the low frequency wave form to mix with the high frequency wave form.

Example 2

Means and Device for Producing Selective Nerve Blockade

In this example we demonstrated that alternate phase pulses of equal amplitude can block the generation and transmission of impulses in nerve fibers. These high frequency, relatively low amplitude (current or voltage) alternate phase pulses can act on the large fibers to flaccidly paralyze skeletal muscles. Higher amplitude pulses are able to produce blockage in small fibers, for example, of the autonomic system. The block is applicable to both afferent and efferent fibers and can be used, for example to block the fibers used in proprioception, pain, and temperature.

During an acute experiment with a canine model, it was demonstrated that high frequency alternate phase pulses applied to sacral nerve roots could produce flaccid paralysis in skeletal muscles. The goal of the experiment was to demonstrate that low amplitude, high frequency sinusoidal currents that are applied to specific sacral roots could reduce the external sphincter pressure of the urethra without effecting the detrusor muscle of the bladder so that voiding might be achieved. The fibers to the detrusor muscle, which are in the same nerve as the fibers to the skeletal muscles, must remain functional so that subsequent electrical stimulation of those fibers would produce enough bladder pressure to assure bladder voiding.

At the onset of stimulation with sinusoidal current (100 Hz), there was an initial contraction of the skeletal muscles indicated by increased sphincter pressure and deflection of the dog's tail. After a few seconds, while the electrical current remained on, the sphincter pressure and the tail deflection subsided. After the skeletal muscles relaxed a higher amplitude lower frequency signal was applied to the same nerve and detrusor contraction was observed without any increase in sphincter pressure. After the sinusoidal current was stopped, the sphincter still responded to low frequency stimulus pulses showing that the paralysis was reversible. Additional tests using monophasic (but charge balanced) rectangular pulses were not able to achieve the same results. Thus, it was demonstrated that relatively high frequency sinusoidal currents were capable of producing reversible flaccid paralysis.

While a sinusoidal current was shown to be the most effective wave form to achieve flaccid paralysis of skeletal muscle, it is not a practical current source for clinical applications. Sinusoidal current requires a large amount of energy when compared with typical present implantable pulse generators which generate very short pulses with relatively long times between (e.g. a 0.2 msec pulse every 50 msec).

Figure 22:
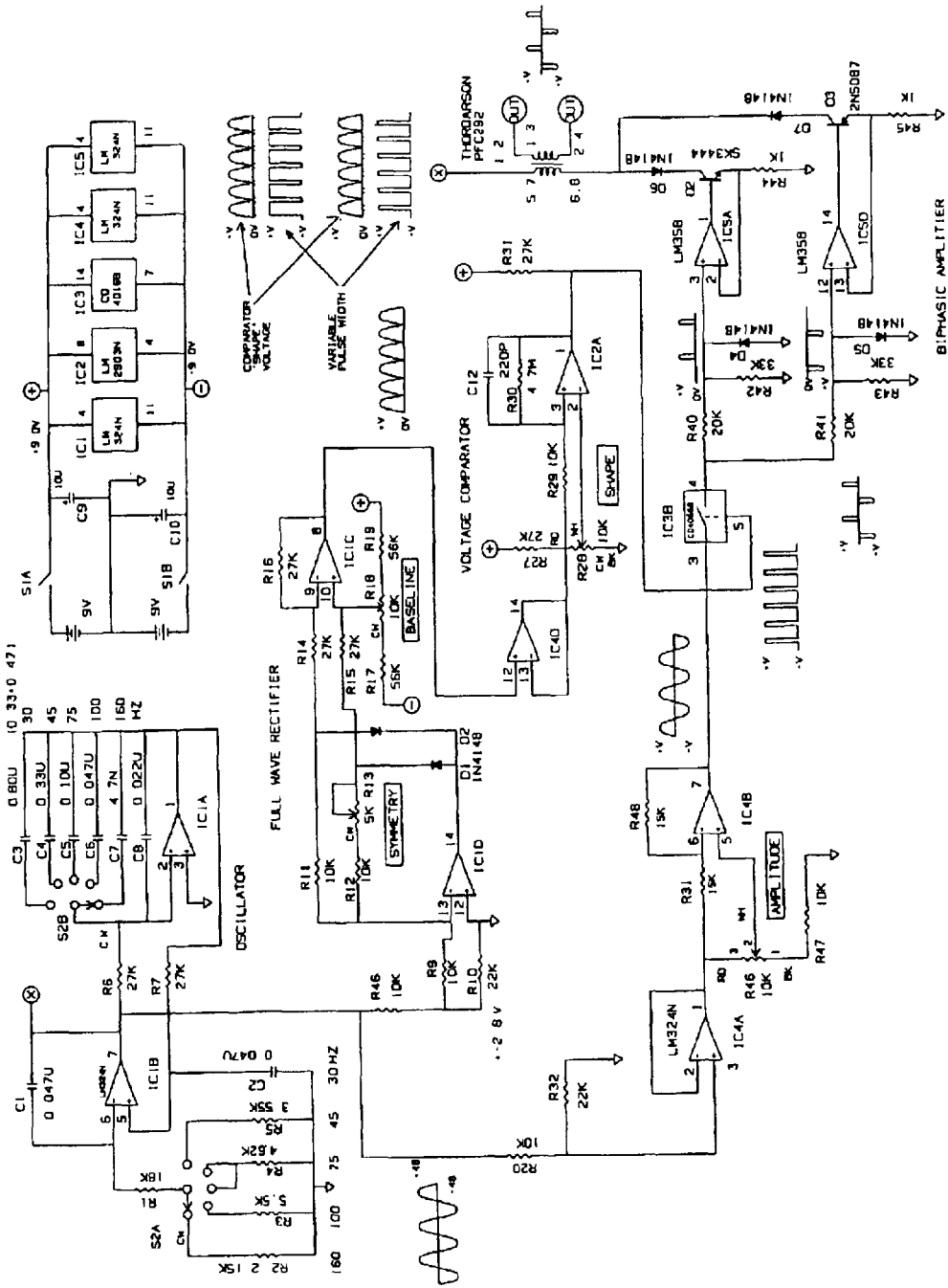
FIG. 22 illustrates one embodiment of a pulse generator suitable for practice of the methods of this invention.

To test whether alternate phase pulse stimulation could result in similar efficacy, a device was built that could trim a full sinusoidal wave into short alternate phase pulses (see, e.g. FIGS. 21 and 22). The change could be accomplished gradually in order to determine how much trimming could occur before the sinusoidal shape no longer produced the flaccid paralysis.

This pulse generator was tested on an acute canine model. The effect of stimulation of the sacral roots with the full sinusoidal wave and the gradually trimmed sinusoidal were compared. Surprisingly, the later was as effective as the former in producing flaccid paralysis of the skeletal muscles. Thus a practical battery-powered implantable pulse generator could be used clinically to obtain flaccid paralysis.

Alternate phase pulses applied at the rate of 100 pulse pairs per second (ppps) to nerve can reversibly block the propagation of impulses. FIG. 21 shows a circuit wave form, and a block diagram of a device that can produce the alternate phase pulses using a single voltage source without an output transformer.

The alternate phase rectangular pulse generator was successfully tested. Although higher frequency pulses are just as effective, the higher frequencies require more energy and are not as practical for clinical use particularly in an implantable device.

Lower frequencies require less energy, but below about 40 or 60 pulse pairs per second do not produce the impulse transmission block. Larger diameter fibers have a lower threshold to impulse initiation than do the smaller diameter fibers, therefore, relatively low amplitudes of current can affect the larger diameter fibers and leave only the small diameter fibers unaffected and remain responsive to higher amplitude lower frequency electrical stimuli.

Blocking the transmission of impulses in the small fibers can be accomplished by using a higher amplitude stimulus current. Although the effect was demonstrated on efferent nerve fibers, the effect is also applicable to afferent nerve fibers. The large sensory fibers that respond to proprioception, for example, could be disabled, while the smaller afferent fibers could continue to respond to stimuli, natural or induced. In addition, higher amplitude alternate phase stimuli applied to the small fibers would block transmission in fibers associated, with pain and temperature.

It is understood that the examples and embodiments described herein are for illustrative purposes only and that various modifications or changes in light thereof will be suggested to persons skilled in the art and are to be included within the purview of this application and scope of the appended claims. All publications, patents, and patent applications cited herein are hereby incorporated by reference in their entirety for all purposes.

What is claimed is:

1. A method of controlling a bladder or a bowel, said method comprising:
applying alternate phase high frequency, low amplitude pulse pairs to a nerve that innervates said bowel or bladder; and
applying alternate phase low frequency, high amplitude pulse pairs to said nerve to void the bladder or bowel, while continuing to apply the alternate phase high frequency, low amplitude pulse pairs.

2. The method of claim 1, wherein the high frequency pulse pairs are at least 50 pulse pairs per second.

3. The method of claim 1, wherein the high frequency pulse pairs range from about 50 to about 200 pulse pairs per second.

4. The method of claim 3, wherein the high frequency pulse pairs range from about 80 to about 120 pulse pairs per second.

5. The method of claim 1, wherein the low frequency pulse pairs are in a range of up to about 40 pulse pairs per second.

6. The method of claim 5, wherein the low frequency pairs are in a range of about 15 to about 25 pulse pairs per second.

7. The method of claim 1, wherein the amplitude of high frequency pulse pairs ranges from about 0.1 milliamperes to about 1.5 milliamperes.

8. The method of claim 1, wherein the amplitude of high frequency pulse pairs ranges from about 0.3 milliamperes to about 0.8 milliamperes.

9. The method of claim 1, wherein the amplitude of low frequency pulse pairs ranges from about 1 milliamperes to about 3 milliamperes.

10. The method of claim 9, wherein the amplitude of low frequency pulse pairs ranges from about 1.3 milliamperes to about 1.7 milliamperes.

11. The method of claim 1, wherein the high frequency pulses have pulse widths in a range of about 0.01 ms to about 0.5 ms.

12. The method of claim 11, wherein the high frequency pulses have pulse widths in a range of about 0.08 ms to about 0.12 ms.

13. The method of claim 1, wherein the low frequency pulses have pulse widths in a range of about 0.1 ms to about 1.0 ms.

14. The method of claim 13, wherein the low frequency pulses have pulse widths of approximately 0.5 ms.

15. A system for controlling a bladder or bowel, said system comprising:
   an electrical pulse generator configured to produce alternate phase high frequency, low amplitude pulses and an alternate phase low frequency, high amplitude pulses to a sacral nerve;
   at least one electrode that can be coupled to a nerve and transmit an electrical signal from said pulse generator to said nerve; and
   an external power source electromagnetically coupled to the electrical pulse generator.

16. The system of claim 15, wherein said electrode is coupled to the sacral nerve and in electrical communication with the electrical pulse generator.

17. The system of claim 15, wherein the system comprises two electrodes coupled to the electrical pulse generator with four wires.

18. The system of claim 15, further comprising a pressure sensitive switch on the electrical pulse generator.

19. A method of controlling a bladder or a bowel, the method comprising:
   providing an electrical pulse generator;
   operatively linking the electrical pulse generator to at least one nerve;
   applying alternate phase high frequency, low amplitude pulse pairs to the nerve; and
   applying low frequency, high amplitude pulse pairs to the nerve to void the bladder while continuing to apply the alternate phase high frequency, low amplitude pulse pairs.

20. The method of claim 19, wherein the high frequency pulse pairs are at least 50 pulse pairs per second.

21. The method of claim 19, wherein the high frequency pulse pairs range from about 50 to about 200 pulse pairs per second.

22. The method of claim 21, wherein the high frequency pulse pairs range from about 80 to about 120 pulse pairs per second.

23. The method of claim 19, wherein the low frequency pulse pairs are in a range of up to about 40 pulse pairs per second.

24. The method of claim 23, wherein the low frequency pairs are in a range of about 15 to about 25 pulse pairs per second.

25. The method of claim 19, wherein the amplitude of high frequency pulse pairs ranges from about 0.1 milliamperes to about 1.5 milliamperes.

26. The method of claim 25, wherein the amplitude of high frequency pulse pairs ranges from about 0.3 milliamperes to about 0.8 milliamperes.

27. The method of claim 19, wherein the amplitude of low frequency pulse pairs ranges from about 1 milliamperes to about 3 milliamperes.

28. The method of claim 27, wherein the amplitude of low frequency pulse pairs ranges from about 1.3 milliamperes to about 1.7 milliamperes.

29. The method of claim 19, wherein the high frequency pulses have pulse widths in a range of about 0.01 ms to about 0.5 ms.

30. The method of claim 19, wherein the high frequency pulses have pulse widths in a range of about 0.08 ms to about 0.12 ms.

31. The method of claim 19, wherein the low frequency pulses have pulse widths in a range of about 0.1 ms to about 1.0 ms.

32. A system for controlling a bladder or bowel, said system comprising:
   an electrical pulse generator configured to produce alternate phase high frequency, low amplitude pulses and an alternate phase low frequency, high amplitude pulses to a sacral nerve;
   at least one electrode that can be coupled to a nerve and transmit an electrical signal from said pulse generator to said nerve; and
   a pressure sensitive switch on the electrical pulse generator.

33. The system of claim 32, wherein said electrode is coupled to the sacral nerve and in electrical communication with the electrical pulse generator.

34. The system of claim 32, wherein the system comprises two electrodes coupled to the electrical pulse generator with four wires.

* * * * *